United States Patent
Yang et al.

(10) Patent No.: US 10,624,874 B2
(45) Date of Patent: Apr. 21, 2020

(54) LASOFOXIFENE MODULATION OF MEMBRANE-INITIATED ESTROGEN SIGNALS AND METHODS FOR TUMOR TREATMENT

(71) Applicant: Zhejiang Jiachi Development Pharmaceuticals LTD, Hangzhou (CN)

(72) Inventors: Jun Yang, Shandong (CN); Wenping Xu, Shanghai (CN)

(73) Assignee: ZHEJIANG JIACHI DEVELOPMENT PHARMACEUTICALS LTD, Hangzhou (CN)

(*) Notice: Subject to any disclaimer, the term of this patent is extended or adjusted under 35 U.S.C. 154(b) by 0 days.

(21) Appl. No.: 16/475,980

(22) PCT Filed: Jan. 10, 2017

(86) PCT No.: PCT/CN2017/070712
§ 371 (c)(1),
(2) Date: Jul. 3, 2019

(87) PCT Pub. No.: WO2018/129645
PCT Pub. Date: Jul. 19, 2018

(65) Prior Publication Data
US 2019/0350901 A1    Nov. 21, 2019

(51) Int. Cl.
| | |
|---|---|
| *A61K 31/40* | (2006.01) |
| *A61P 35/00* | (2006.01) |
| *A61K 31/444* | (2006.01) |
| *A61K 31/506* | (2006.01) |
| *A61K 31/517* | (2006.01) |
| *A61K 31/519* | (2006.01) |
| *A61K 31/5377* | (2006.01) |
| *A61K 39/395* | (2006.01) |

(52) U.S. Cl.
CPC .......... *A61K 31/40* (2013.01); *A61K 31/444* (2013.01); *A61K 31/506* (2013.01); *A61K 31/517* (2013.01); *A61K 31/519* (2013.01); *A61K 31/5377* (2013.01); *A61K 39/3955* (2013.01); *A61P 35/00* (2018.01); *A61K 2300/00* (2013.01)

(58) Field of Classification Search
CPC ...................................................... A61K 31/40
USPC ............................................................ 514/408
See application file for complete search history.

(56) References Cited

U.S. PATENT DOCUMENTS

| | | |
|---|---|---|
| 10,231,978 B2 | 3/2019 | Yang et al. |
| 2014/0134170 A1 | 5/2014 | Garcia et al. |

FOREIGN PATENT DOCUMENTS

| | | |
|---|---|---|
| CN | 103562226 A | 2/2014 |
| WO | WO-2008/145075 A2 | 12/2008 |
| WO | WO-2008/145075 A3 | 3/2009 |
| WO | WO-2009/126662 A1 | 10/2009 |
| WO | WO-2015/169173 A1 | 11/2015 |
| WO | WO-2018/129645 A1 | 7/2018 |
| WO | WO-2019/041078 A1 | 3/2019 |
| WO | WO-2019/042192 A1 | 3/2019 |

OTHER PUBLICATIONS

Barry, W. T. et al. (May 1, 2005, e-pub. Jan. 10, 2005). "Significance analysis of functional categories in gene expression studies: a structured permutation approach", *Bioinformatics* 21(9):1943-1949.
Boonyaratanakornkit, V. (Aug. 2011, e-pub. Feb. 25, 2011). "Scaffolding proteins mediating membrane-initiated extra-nuclear actions of estrogen receptor", *Steroids* 76(9):877-884.
Bouchardy, C. et al. (Mar. 15, 2011, e-pub. Jan. 24, 2011). "Lung cancer mortality risk among breast cancer patients treated with anti-estrogens", *Cancer* 117(6):1288-1295, 9 pages.
Bravo, R. et al. (Jul. 1, 2011). "Increased ER-mitochondrial coupling promotes mitochondrial respiration and bioenergetics during early phases of ER stress", *J Cell Sci.* 124(13):2143-2152.
Bussemaker, H.J. (2007, e-pub. Sep. 27, 2007). "Dissecting complex transcriptional responses using pathway-level scores based on prior information", *BMC Bioinformatics* 8(Suppl 6):S6, 7 pages.
Butler, W.B. (Jan. 1981). "Effects of serum and insulin on the sensitivity of the human breast cancer cell line MCF-7 to estrogen and antiestrogens", *Cancer Res.* 41(1):82-88.
Cesarone, G. et al. (May 15, 2006). "RNAi-mediated silencing of insulin receptor substrate 1 (IRS-1) enhances tamoxifen-induced cell death in MCF-7 breast cancer cells", *J Cell Biochem.* 98(2):440-450.
Chandanos, E. et al. (Jul. 3, 2006, e-pub. Jun. 27, 2006). "Tamoxifen exposure and risk of oesophageal and gastric adenocarcinoma: a population based cohort study of breast cancer patients in Sweden", *Br J Cancer* 95(1):118-122.
Cummings, S.L. et al. (Feb. 25, 2010). "Lasofoxifene in Postmenopausal Women with Osteoporosis", *The New England Journal of Medicine* 362(8):686-696.
Duell E.J. et al. (Dec. 15, 2010, e-pub. Nov. 4, 2010). "Menstrual and reproductive factors, exogenous hormone use, and gastric cancer risk in a cohort of women from the European Prospective Investigation Into Cancer and Nutrition", *Am J Epidemiol* 172(12):1384-1393.
Fernandez, E. et al (Jun. 20, 2003). "Hormone replacement therapy and cancer risk: a systematic analysis from a network of case control studies", *Int J Cancer* 105(3):408-412, 17 pages.

(Continued)

*Primary Examiner* — Raymond J Henley, III
(74) *Attorney, Agent, or Firm* — Morrison & Foerster LLP

(57) ABSTRACT

The present invention found that lasofoxifene is an antagonist of ER-α36. It not only inhibits the growth of ER-α36 positive lung, colon and gastric cancers, and also it can inhibit the growth of acquired or de novo tamoxifen-resistant MCF-7 cells. Our finding also provides methods and compositions for treating cancer comprising lasofoxifene alone or in combination with at least one other agent selected from the group consisting of gefitinib and/or trastuzumab or functional equivalent thereof, and an inhibitor in hormonal or epidermal growth factor signal transduction pathways.

20 Claims, 12 Drawing Sheets

(56) References Cited

OTHER PUBLICATIONS

Frise, S. et al. (Dec. 2006, e-pub. Jul. 13, 2006). "Menstrual and reproductive risk factors and risk for gastric adenocarcinoma in women: findings from the Canadian national enhanced cancer surveillance system", *Ann Epidemiol* 16(12):908-916.

Gennari, L. et al. (Jun. 2006). "Lasofoxifene: a new type of selective estrogen receptor modulator for the treatment of osteoporosis", *Drugs Today (Barc)* 42(6):355-367.

International Search Report dated Oct. 17, 2017, for Patent Application No. PCT/CN2017/070712, filed Jan. 10, 2017, 5 pages.

Kaneko, S. et al (Feb. 2003). "Menstrual and reproductive factors and the mortality risk of gastric cancer in Japanese menopausal females", *Cancer Causes Control* 14(1):53-59.

Kang, L. et al. (Apr. 2010, e-pub. Mar. 2, 2010). "Involvement of estrogen receptor variant ER-alpha36, not GPR30, in nongenomic estrogen signaling", *Mol Endocrinol.* 24(4):709-721, 21 pages.

Ke, H.Z. et al. (Apr. 1998). "Effects of CP-336,156, a new, nonsteroidal estrogen agonist/antagonist, on bone, serum cholesterol, uterus and body composition in rat models", *Endocrinology* 139(4):2068-2076.

Kelly, M.J. (May-Jun. 2001). "Rapid actions of plasma membrane estrogen receptors", *Trends Endocrinol Metab.* 12(4):152-156.

Kiyohara, C. (Oct. 2010). "Sex differences in lung cancer susceptibility: a review", *Gender Medicine* 7(5):381-401.

Lasofoxifene (CAS#180916-16-9), PubChem Database CID 216416, National Center for Biotechnology Information, located at: https://pubchem.ncbi.nlm.nih.gov/compound/Lasofoxifene (accessed on Jul. 9, 2019), 21 pages.

Lindblad, M. et al. (Dec. 2004). "Estrogen and risk of gastric cancer: a protective effect in a nationwide cohort study of patients with prostate cancer in Sweden", *Cancer Epidemiol Biomarkers Prev* 13(12):2203-2207.

Lindblad, M. et al. (Jan. 16, 2006, e-pub. Jan. 10, 2006). "Hormone replacement therapy and risks of oesophagea and gastric adenocarcinomas", *Br J Cancer* 94(1):136-141.

Maglietta, R. et al. (Aug. 15, 2007, e-pub. May 31, 2007). "Statistical assessment of functional categories of genes deregulated in pathological conditions by using microarray data", *Bioinformatics* 23(16):2063-2072.

Mårtensson, U.E. et al. (Feb. 2009, Oct. 9, 2008). "Deletion of the G protein-coupled receptor 30 impairs glucose tolerance, reduces bone growth, increases blood pressure, and eliminates estradiol-stimulated insulin release in female mice", *Endocrinology* 150(2):687-698.

Matsuyama, Y. et al (Dec. 2000). "Second cancers after adjuvant tamoxifen therapy for breast cancer in Japan", *Ann Oncol.* 11(12):1537-1543.

Mauvais-Jarvis, F. et al. (Jun. 2013, e-pub. Mar. 4, 2013). "The role of estrogens in control of energy balance and glucose homeostasis", *Endocr Rev.* 34(3):309-38, 48 pages.

Mocellin, S. et al. (Nov. 18, 2015, e-pub. Feb. 2016). "Breast Cancer Chemoprevention: A Network Meta-Analysis of Randomized Controlled Trials", *J Natl Cancer Inst.* 108(2):djv318, 9 pages.

Nehra, R. et al. (Jun. 2010). "BCL2 and CASP8 regulation by NF-kappaB differentially affect mitochondrial function and cell fate in antiestrogen-sensitive and -resistant breast cancer cells", *FASEB J.* 24(6):2040-2055, 28 pages.

Nilsson, B.O. et al. (Jul. 2011). "G protein-coupled oestrogen receptor 1 (GPER1)/GPR30: a new player in cardiovascular and metabolic oestrogenic signaling", *Br. J. Pharmacol.* 163(6):1131-1139.

Novak, B. A. et al. (Jan. 15, 2006, e-pub. Nov. 8, 2005). "Pathway recognition and augmentation by computational analysis of microarray expression data", *Bioinformatics* 22(2):233-241.

Prossnitz, E.R. et al. (May 25, 2014, e-pub. Feb. 12, 2014). "Estrogen biology: new insights into GPER function and clinical opportunities", *Mol, Cell Endocrinol.* 389(1-2):71-83.

Ramchandran, K. et al. (Dec. 2009). "Sex Differences in Susceptibility to Carcinogens", *Semin. Oncol.* 36(6):516-523.

Rao, J. et al. (Nov. 2011, e-pub. Aug. 22, 2011). "Advances in the understanding of the structure and function of ER-α36, a novel variant of human estrogen receptor-alpha", *J Steroid Biochem Mol. Biol.* 127(3-5):231-237.

Revankar, C.M. et al. (Mar. 11, 2005, Feb. 10, 2005). "A transmembrane intracellular estrogen receptor mediates rapid cell signaling", *Science* 307(5715):1625-1630.

Segal, E. et al. (Jun. 2003). "Module networks: identifying regulatory modules and their condition-specific regulators from gene expression data", *Nat. Genet.* 34(2):166-176.

Segal, E. et al. (Oct. 2004, e-pub. Sep. 26, 2004). "A module map showing conditional activity of expression modules in cancer", *Nat. Genet.* 36(10):1090-1098.

Shi, L. et al. (Jul. 20, 2009, e-pub. Jun. 1, 2009). "Expression of ER-α36, a Novel Variant of Estrogen Receptor α, and Resistance to Tamoxifen Treatment in Breast Cancer", *J. Clin. Oncol.* 27(21):3423-3429.

Shi, L.et al. (2014, e-pub. Mar. 16, 2014). "Regulatory mechanisms of betacellulin in CXCL8 production from lung cancer cells", *J Transl Med* 12:70, 11 pages.

Shibata, Y. et al. (Aug. 11, 2006). "Rough sheets and smooth tubules", *Cell* 126(3):435-439.

Sipponen, P. et al. (2002). "Delayed rise in incidence of gastric cancer in females results in unique sex ratio (M/F) pattern: etiologic hypothesis", *Gastric Cancer* 5(4):213-219.

Tian, L. et al. (Sep. 20, 2005, e-pub. Sep. 8, 2005). "Discovering statistically significant pathways in expression profiling studies", *PNAS USA* 102(38):13544-13549.

U.S. Appl. No. 16/626,617, filed Jan. 30, 2019, by Yang et al. (A copy of the U.S. Patent Application is not submitted herewith pursuant to the waiver of 37 C.F.R. § 1.98(a)(2)(iii) issued by the Office on Sep. 21, 2004).

Wang, J. et al. (Jan. 2012, e-pub. Oct. 12, 2011). "Expression of ER α36 in gastric cancer samples and in their matched normal tissues", *Oncol Lett.* 3(1):172-175.

Wang, Z. et al. (Nov. 4, 2005). "Identification, cloning, and expression of human estrogen receptor-α 36, a novel variant of human estrogen receptor-α66", *Biochem Biophys Res Commun* 336(4):1023-1027.

Wang, Z.Y. et al. (Jun. 13, 2006, e-pub. Jun. 5, 2006). "A variant of estrogen receptor-α, hER-α36: Transduction of estrogen- and antiestrogen-dependent membrane-initiated mitogenic signaling", *PNAS USA* 103(24):9063-9068.

White, C. et al. (Oct. 2005, e-pub. Sep. 18, 2005). "The endoplasmic reticulum gateway to apoptosis by Bcl-X(L) modulation of the InsP3R", *Nat Cell Biol.* 7(10):1021-1028.

Written Opinion of the International Search Opinion dated Oct. 17, 2017, for Patent Application No. PCT/CN2017/070712, filed Jan. 10, 2017, 6 pages.

Xie Xin-ci et al. (Dec. 31, 2015). "Advances in Research of Estrogen Receptor in Tumor Development" *Pharmaceutical Biotechnology* 22(2):156-159. (English Abstract Only).

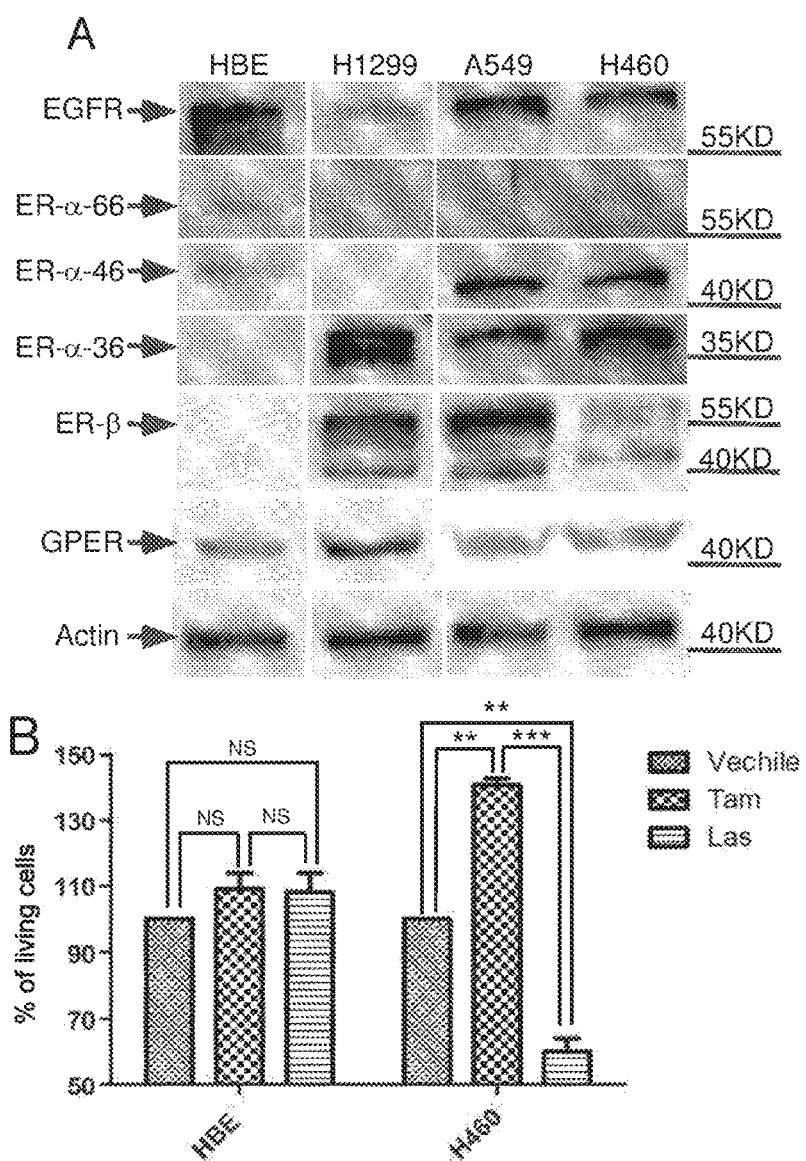
Figure 5: Parts A and B

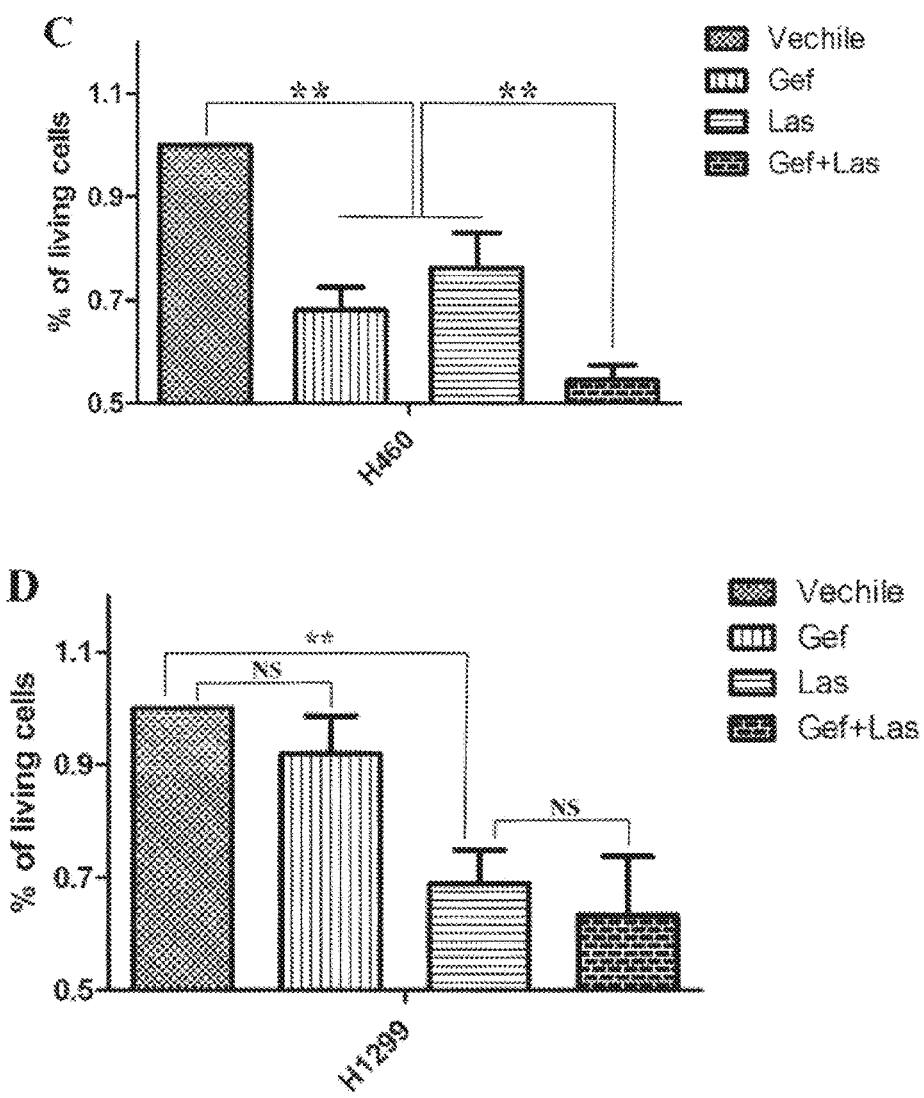
Figure 5; Parts C and D

LASOFOXIFENE MODULATION OF MEMBRANE-INITIATED ESTROGEN SIGNALS AND METHODS FOR TUMOR TREATMENT

CROSS-REFERENCE TO RELATED APPLICATIONS

This application is the U.S. national phase application under 35 U.S.C. § 371 of International Application No. PCT/CN2017/070712, filed on Jan. 10, 2017.

TECHNICAL FIELD

The present invention relates to methods of treating cancers positively expressing estrogen receptor alpha-36 (ER-α36) using lasofoxifene or a combination of lasofoxifene with a protein kinase inhibitor, or functional equivalent thereof, such as gefitinib or trastuzumab.

BACKGROUND OF THE INVENTION

Decreased production of estrogen in the postmenopausal women leads to symptoms such as osteoporosis and fat liver, etc. Estrogen replacement therapy has been utilized to treat these symptoms and showed an increased risk of breast and uterine cancers. Marketed as an antagonist of estrogen receptor (ER) to treat ER$^+$ breast cancer patients, tamoxifen also induces de novo or acquired tamoxifen resistance resulting in the discovery of estrogen classic nuclear pathway, the membrane-initiated estrogen receptors and their signal transduction pathways.

Previously, epidemiologic data demonstrated that women had a higher risk of non-small cell lung cancer (NSCLC) compared with men after excluding smoking effect, and a lower risk of lung cancer mortality compared with that in breast cancer patients treated by antiestrogenic therapy. Similarly, the epidemiological studies of gastric cancer incidence indicate the higher gastric cancer in males than females prior to menopause, however, following menopause, there is no significant difference of incidence between females and males. In prostate cancer patients, the higher risk of gastric cancer has been reported, which is decreased when those patient were treated by antiestrogenic medicine. In breast cancer ER$^+$ patients whose cancer, a significantly increased risk of subsequent gastric cancer was reported when the patients were treated by tamoxifen. In addition, ovariectomy (OVX) also significantly increases the risk of gastric cancer in females. Taken together, estrogen possibly plays an important role in the development of NSCLC and gastric cancers.

Three genes encoding estrogen-bound proteins have been identified: G-protein coupled estrogen receptor 1 (GPER1 or GPR30), estrogen receptor-α (ER-α) and estrogen receptor-β(ER-β), which have similar structural and functional domains, including activation function domain 1 (AF-1), a DNA binding domain (DBD), a dimerization domain and activation function domain 2 (AF-2), which is the ligand binding domain (LBD). ER-α and ER-β, both belonging to the nuclear super family of ligand-dependent transcription factors, have highly conserved DBD and LBD regions modulating the classical nuclear estrogen pathway. Insulin (IL) binds to insulin receptor (IR), stimulating the phosphorylation of insulin receptor substrate (IRS); that phosphorylated IRS interacts with dimer estrogen-ER complexes, which can then translocate into the nucleus and bond with estrogen response elements (ERE) sequence to regulate RNA transcription through the estrogen classical nuclear pathway. Bcl-2, a key member of anti-apoptosis family proteins, has been reported to have its over-expression linked to many kinds of cancers in human being. The promoter of Bcl-2 gene contains an ERE sequence, and Bcl-2 mRNA expression in MCF-7 cells has been found to be positively regulated by E2 (17β-estradiol, an estrogen) and inhibited by tamoxifen; and that the proliferation of MCF-7 cells is modulated by IL, and the sensitivity of these cells to tamoxifen is increased after the temporary removal of IL from culture medium or when IRS expression was transiently knocked down using IRS-specific siRNA.

ER-α and ER-β also regulate cell proliferation, matrix/migration, metabolism and glucose homeostasis through membrane-initiated estrogen signaling (MIES), associating with plasma membrane by palmitoylation interaction in their LBD. The previous studies on ER knockout mice indicate that ER-α is the dominant functional estrogen receptor, when compared with ER-β. Clinically, ER positive cancers are diagnosticated by the ER-α antibody. Three transcription variants of ER-α66, 46 and 36, have been found. ER-α36 contains a partial ligand binding domain and palmitoylation motif (445-453), and possessing a unique C-terminal 27 amino acid sequence in place of the typical 140 amino acids (456-595) of full-length ER-α. ER-α36 has been found to be located predominantly at plasma membrane using an ER-α36 specific antibody. Since ER-α36 lacks the AF-1 and AF-2 domains, and that it still contains the ability binding to membrane, moreover, it is found to be uniquely expressed in tamoxifen-resisted breast cancer cells and uterine endometria epithelia cancer cells, MIES modulated by membrane-bound ER-α36 is thought to be responsible for the resistance to the anti-estrogen therapy. The previous studies demonstrated that the expression of ER-α36 may be one of the factors affecting tumorigenesis in gastric cancer patients. Moreover, because previously known ER-α antibodies could not effectively recognize ER-α36, an ER-α36 specific antibody was developed by investigators. See e.g., Wang Z. Y. et al., *Proc. Natl. Acad. Sci. USA*. 2006, 103(24):9063-8. Using the ER-α36 specific antibody, investigators found that ER-α36 was overexpressed in triple negative breast cancers and in acquired or de novo tamoxifen-resistant ER-positive breast cancers. See Shi, et al., *J. Clin. Oncol.* 2009, 27(31), 3423-9.

GPER1 has been found predominately on endoplasmic reticular. It binds with E2 to modulate sensitive Ca$^{2+}$ signal through G protein alpha subunit (Gas). E2-GPER1 complex actives Gas/PLC/inositol trisphosphate (IP$_3$) pathway, which subsequently promotes Ca$^{2+}$ release from Inositol 1, 4, 5-Trisphosphate Receptors (InsP$_3$R) enhancing cell bioenergetics and apoptosis resistance. GPER1 knockout mice have been reported to exhibit impaired glucose tolerance, reduced bone growth, increased blood pressure, and eliminated estradiol-stimulated insulin release to cardiovascular, with no apparent effect on fertility. Thus, GPER1 involved in the modulation of estrogen-mediated metabolic signaling.

Raloxifene, lasofoxifene, bazedoxifene, or functional equivalent selective estrogen receptor modulators (SERM) were developed to prevent osteoporosis for postmenopausal women. A network meta-analysis of randomized controlled trials showed that these SERMs have a better benefit-risk ratio than that of aromatase inhibitors and tamoxifen (Mocellin, et al, *J. Natl. Cancer Inst.* 2016, 108(2):djv318).

There remains a need for a safe and effective treatment of cancers, in particular tamoxifen-resistant cancers.

BRIEF SUMMARY OF THE INVENTION

In one aspect, the invention provides a method of treating cancer in an individual comprising administering to the individual an effective amount of lasofoxifene, or a pharmaceutically acceptable salt thereof, wherein the cancer is an ER-α36 positive cancer.

The method is for treating any cancer expressing ER-α36, such as any solid tumors expressing ER-α36, including but not limited to, breast cancer, uterine endometrial cancer, lung cancer, gastric cancer, colon cancer, pancreatic cancer, thyroid cancer and liver cancer; or any liquid tumors expressing ER-α36, such as chronic lymphocytic leukemia (CLL).

In some embodiments, the cancer is a breast cancer. In some embodiments, the cancer is a tamoxifen-resistant breast cancer, wherein the resistance to tamoxifen may be de novo or acquired. In some embodiments, the ER-α36 positive breast cancer is a triple negative breast cancer.

In some embodiments, the cancer is a lung cancer (e.g., NSCLC). In some embodiments, the cancer is a nuterine endometrial cancer. In some embodiments, the cancer is a gastric cancer. In some embodiments, the cancer is a colon cancer. In some embodiments, the cancer is a pancreatic cancer. In some embodiments, the cancer is a liver cancer. In some embodiments, the cancer is a thyroid cancer. In some embodiments, the cancer is CLL.

In some embodiments, the ER-α36 positive cancer is also an EGFR positive cancer, for example, an EGFR positive breast cancer or an EGFR positive lung cancer. Where the ER-α36 positive cancer is also EGFR positive, the method may further comprise administering to the individual an EGFR kinase inhibitor. In some embodiments, lasofoxifene or pharmaceutically acceptable salt thereof and the EGFR kinase inhibitor are administered simultaneously. In some embodiments, lasofoxifene or pharmaceutically acceptable salt thereof and the EGFR kinase inhibitor are administered sequentially. Any EGFR kinase inhibitor may be co-administered with lasofoxifene or pharmaceutically acceptable salt thereof, such as, including but not limited to, gefitinib, erlotinib, icotinib, afatinib, neratinib, dacomitinib, osimertinib, rociletinib orlmutinib, or a pharmaceutically acceptable salt thereof.

In some embodiments, the ER-α36 positive cancer is also a HER2 positive cancer, for example, a HER2 positive breast cancer or a HER2 positive gastric cancer. Where the ER-α36 positive cancer is also HER2 positive, the method may further comprise administering to the individual an HER2 inhibitor. In some embodiments, lasofoxifene or pharmaceutically acceptable salt thereof and the HER2 inhibitor are administered simultaneously. In some embodiments, lasofoxifene or pharmaceutically acceptable salt thereof and the HER2 inhibitor are administered sequentially. Any HER2 inhibitor may be co-administered with lasofoxifene or pharmaceutically acceptable salt thereof, such as, including but not limited to, trastuzumab, pertuzumab, lapatinib or ado-trastuzumab emtansine (T-DM1). In some embodiments, the HER2 inhibitor is an anti-HER2 antibody.

Also provided is a method of treating an ER-α36 positive cancer in an individual comprising administering to the individual: a) an effective amount of lasofoxifene or a pharmaceutically acceptable salt thereof; and optionally b) an effective amount of at least one other agent selected from the group consisting of a phosphorylation kinase inhibitor of epithelia growth factor receptor such as EGFR phosphorylation inhibitor (e.g., gefitinib) or functional equivalent thereof, and an inhibitor of epithelia growth factor receptor such as trastuzumab (e.g., Herceptin®) or a functional equivalent thereof.

In some embodiments, the cancer is selected from the group consisting of breast cancer, uterine endometrial cancer, lung cancer, pancreatic cancer, gastric cancer, colon cancer, liver cancer, thyroid cancer and CLL etc. whose cells positively express ER-α36. In some embodiments, the ER-α36 positive breast cancer is resistant to treatment with tamoxifen. In some embodiments, the ER-α36 positive uterine endometrial cancer is resistant to treatment with tamoxifen.

In some aspects of the method of treating an ER-α36 positive cancer may further comprise determining ER-α36 expression in the cancer, for example, by the presence of an ER-α36 peptide and/or the presence of ER-α36 mRNA. In some embodiments, ER-α36 expression in the cancer is determined by presence of an ER-α36 peptide, for example, as measured by an immuno-hybridization method (e.g., western blotting, immuno-histological or -fluorescence staining). In some embodiments, ER-α36 expression in the cancer is determined by presence of an ER-α36 mRNA, for example, as measured by quantitative polymerase chain reaction (q-PCR).

In some embodiments, the individual is human.

Further provided is a pharmaceutical composition comprising an effective amount of lasofoxifene, or a pharmaceutically acceptable salt thereof, and at least one additional agent selected from the group consisting of an EGFR kinase inhibitor (e.g., gefitinib, erlotinib, icotinib, afatinib, neratinib, dacomitinib, osimertinib, rociletinib or olmutinib, or a pharmaceutically acceptable salt thereof) or a functional equivalent thereof, and a HER2 inhibitor (e.g., trastuzumab, pertuzumab, lapatinib, or ado-trastuzumab emtansine (T-DM1), or a pharmaceutically acceptable salt thereof) or a functional equivalent thereof.

The pharmaceutical composition can be present in a unit dosage formula, for example an oral unit dosage formula, such as capsules, tablets, pills, caplets, gels, liquids (e.g., suspensions, solutions, emulsions), powders or other particulates, and so forth. In some embodiments, the dosage of lasofoxifene is about 0.25-50 mg per day.

In another aspect, the invention provides a kit comprising (i) a composition comprising lasofoxifene or a pharmaceutically acceptable salt thereof; and (ii) an agent for determining presence of an ER-α36 peptide or ER-α36 mRNA. In some embodiments, the kit comprises an agent for determining presence of an ER-α36 peptide, for example, an antibody recognizing the ER-α36 peptide. In some embodiments, the kit comprises an agent for determining presence of an ER-α36 mRNA, for example, an oligonucleotide for quantitative measurement of ER-α36 mRNA.

Also provided is lasofoxifene, or a pharmaceutically acceptable salt thereof, for use in a method for the treatment of an ER-α36 positive cancer, such as an ER-α36 positive cancer detailed herein. In some embodiments, provided is a combination of lasofoxifene, or a pharmaceutically acceptable salt thereof, with another agent selected from the group consisting of tamoxifen or functional equivalent thereof, an EGFR kinase inhibitor (e.g., gefitinib) or a functional equivalent thereof, and a HER2 inhibitor (e.g., trastuzumab) or a functional equivalent thereof, for the treatment of an ER-α36 positive cancer, wherein the cancer also expresses a biomarker such as an EGFR kinase or HER2.

Also provided is a use of lasofoxifene, or a pharmaceutically acceptable salt thereof, in the manufacture of a medicament for the treatment of an ER-α36 positive cancer, such as an ER-α36 positive cancer detailed herein. In some embodiments, provided is a use of a combination of lasofoxifene, or a pharmaceutically acceptable salt thereof, with another agent selected from the group consisting of tamoxifen or functional equivalent thereof, an EGFR kinase inhibitor (e.g., gefitinib) or a functional equivalent thereof, and a HER2 inhibitor (e.g., trastuzumab) or a functional equivalent thereof, in the manufacture of a medicament for the treatment of an ER-α36 positive cancer, wherein the cancer also expresses a biomarker such as an EGFR kinase or HER2.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE FIGURES

FIG. 5: Inhibition of proliferation of ER-α36 positive/EGFR positive lung cancer cells by a combination of lasofoxifene and gefitinib. A. Cell lines HBE, H1299 and H460 were cultured. Expression of EGFR, ER-α66, ER-α46, ER-α36, ER-β, GPER-1 were tested using Western blot. B. HBE cells and H460 cells were treated with 2 μM tamoxifen or 2 μM lasofoxifene. Proliferation of HBE cells and H460 cells were shown after each treatment. C. H460 cells were treated with vehicle only, or gefitinib, or lasofoxifene, or a combination of gefitinib and lasofoxifene. Proliferation of MCF-7 were shown after each treatment. D. H1299 were treated with vehicle only, or gefitinib, or lasofoxifene, or a combination of gefitinib and lasofoxifene. Proliferation of lung cancer cells was shown after each treatment. N=3×3; ** means $P<0.01$; NS: non-significantly different; LAS: lasofoxifene; and Gef: gefitinib.

DETAILED DESCRIPTION OF THE INVENTION

Figure 1:
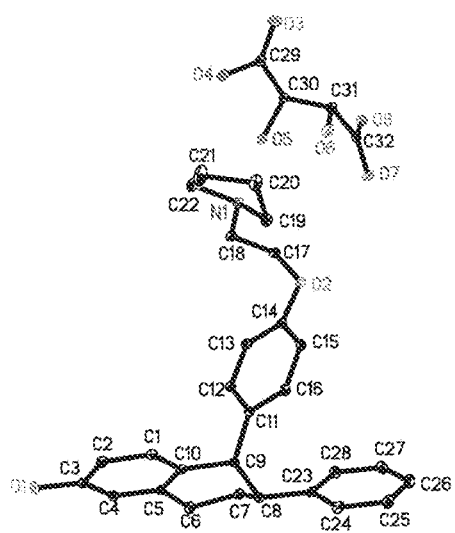
FIG. 1: co-crystal structure of lasofoxifene with (2S,3S)-2,3-dihydroxybutanedioate (D-tartrate).

The present disclosure provides methods and compositions for therapy comprising lasofoxifene alone or in conjunction with a second agent for treatment of cancer through inhibition of ER-α36-induced cell proliferation signal pathway, and reducing osteoporosis via active GPER1.

Definitions

The methods described herein are generally useful for treatment of diseases. As used herein, "treatment" is an approach for obtaining beneficial or desired clinical results. For example, for treatment of cancer, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delaying or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

Individuals having "triple negative breast cancer" used herein refer to individuals who are clinically negative for expression of estrogen receptor (ER), progesterone receptors (PR) and HER2 protein.

"mER" refers to membrane-bound estrogen receptor. ER was anchored on the plasma membrane through the palmitoylation modification at a Cysteine residue of its estrogen binding domain (LBD). ER-α36 is a truncated ER-α variant. It remains palmitoylation motif (445-453) and possesses a unique 27 amino acid instead of 140 amino acid region (456-595) of full length ER-α at C-terminus. Since ER-α36 possesses a partial LBD and predominantly localizes at plasma membrane and cytosol, it does not bind with estrogen resulting in losing the modulating ability of estrogen classical pathway.

"mER positive" "EGFR positive," "HER2 positive" used herein refer to individuals who are clinically positive for membrane-bound estrogen receptor, epidermal growth factor receptor (EGFR), or human epidermal growth factor receptor 2 (HER2), respectively. "ER-α36 positive" used herein refer to individuals who are clinically positive for the ER-α36 variant.

An individual is considered "clinically positive" for a biomarker when the level of the biomarker in tumor cells in a biopsy specimen of the individual is higher than that in normal tissue cells in the biopsy specimen of the individual as experimentally determined. None limiting examples of experimental techniques for determining the level of biomarkers include qPCR, immunohistochemistry (IHC) or immunofluorescence (IF) staining and Western blotting (WB). For example, in an ER-α36 positive individual, the level of the ER-α36 variant in tumor cells in a biopsy specimen of the individual is higher than that in normal tissue cells in the biopsy specimen of the individual as experimentally determined, for example, using methods described in Shi, et al., *J. Clin. Oncol.* 2009, 27(31), 3423-9. In some embodiments, an ER-α36 positive individual has an ER-α36 level in tumor cells in a biopsy specimen that is at least 25% higher than that in normal tissue cells in the biopsy specimen, as measured by IHC, IF or WB methods. In some embodiments, an ER-α36 positive individual has an ER-α36 mRNA level in tumor cells in a biopsy specimen that is at least 50% higher than that in normal tissue cells in the biopsy specimen, as measured by qPCR. A low level ER-α36 positive individual has an ER-α36 level in tumor cells in a biopsy specimen that is about 25% to about 100% higher than that in normal tissue cells in the biopsy specimen, as measured by IHC, IF or WB methods; or has an ER-α36 mRNA level in tumor cells in a biopsy specimen that is about 50% to about 100% higher than that in normal tissue cells in the biopsy specimen, as measured by qPCR. A high level ER-α36 positive individual has an ER-α36 level in tumor cells in a biopsy specimen that is 100% or more higher than that in normal tissue cells in the biopsy specimen, as measured by qPCR, IHC, IF or WB methods.

The term "effective amount" used herein refers to an amount of a compound or composition sufficient to treat a specified disorder, condition or disease such as ameliorate, palliate, lessen, and/or delay one or more of its symptoms. In reference to cancers, an effective amount comprises an amount sufficient to cause a tumor to shrink and/or to decrease the growth rate of the tumor (such as to suppress tumor growth) or to prevent or delay other unwanted cell proliferation.

The term "individual" is a mammal, including humans. An individual includes, but is not limited to, human, bovine, horse, feline, canine, rodent, or primate. In some embodiments, the individual is human.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Lasofoxifene

Lasofoxifene, (−)-cis-(5R,6S)-6-phenyl-5-[4-(2-pyrrolidin-1-ylethoxy)phenyl]-5,6,7,8-tetrahydronaphthalen-2-ol, CAS #180916-16-9, has the following chemical structure:

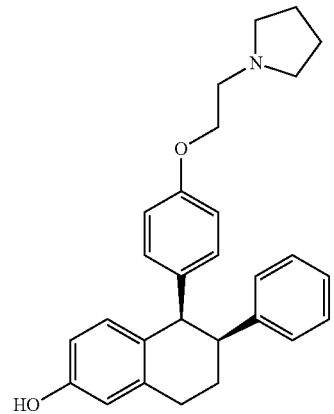 [SMILES: Oc1ccc2c(c1)CC[C@H](c1ccccc1)[C@@H]2c1ccc(OCCN2CCCC2)cc1]

The pure enantiomer has been obtained by the tartrate split method (co-crystallization with D-tartrate). The absolute configuration has been confirmed by X-ray crystallography of a co-crystal with D-tartrate. Lasofoxifene is a selective estrogen receptor modulator, and has high binding affinity to ER-α.

In some embodiments of the methods and compositions detailed herein, a pharmaceutically acceptable salt of lasofoxifene is used. A "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. Non-limiting examples of pharmaceutically acceptable positive counter ions include sodium, potassium, calcium, magnesium, ammonium, tetraalkylammonium, and the like. Non-limiting examples of pharmaceutically acceptable negative counter ions include chloride, bromide, formate, tartrate, besylate, mesylate, acetate, maleate, oxalate, and the like.

Methods

Without wishing to be bound by theory, the invention is based, in part, on the discovery of the unique properties and mechanism of actions of selective estrogen membrane-initiated modulators such as lasofoxifene and raloxifene. After screening, we surprisingly found that lasofoxifene is an antagonist of ER-α36 that inhibits cancer cell division. On the other hand, lasofoxifene and raloxifene can function as an agonist on the GPER1 pathway, which modulates metabolic signals in bone. The beneficial effects of lasofoxifene thus include: i) the inhibition of malignant cell growth regulated by membrane-associated estrogen receptor alpha (ER-α) such as ER-α36, ii) the modulation of estrogen metabolic effect as GPER1 agonist which leads to reduction of postmenopausal symptoms such as osteoporosis.

In one aspect, the present invention provides a method of treating cancer in an individual comprising administering to the individual an effective amount of lasofoxifene, or a pharmaceutically acceptable salt thereof, wherein the cancer is an ER-α36 positive cancer.

The method is useful for treating any cancer expressing ER-α36 (or ER-α36 positive cancer), such as any solid tumors expressing ER-α36 (or ER-α36 positive solid tumor), including but not limited to, breast cancer, uterine endometrial cancer, lung cancer, gastric cancer, colon cancer, pancreatic cancer, thyroid cancer and liver cancer; or any liquid tumor expressing ER-α36 (or ER-α36 positive liquid tumor), such as chronic lymphocytic leukemia (CLL).

In some embodiments, the cancer is a breast cancer. In some embodiments, the cancer is a tamoxifen-resistant breast cancer, wherein the resistance to tamoxifen may be de novo or acquired. In some embodiments, the ER-α36 positive breast cancer is a triple negative breast cancer. In some embodiments, the uterine endometrial cancer is at a moxifen-induced uterine endometrial cancer.

In some embodiments, the cancer is a lung cancer (e.g., small cell lung cancer and non-small cell lung cancer (NSCLC)). In some embodiments, the cancer is an uterine endometrial cancer. In some embodiments, the cancer is a gastric cancer. In some embodiments, the cancer is a colon cancer. In some embodiments, the cancer is a pancreatic cancer. In some embodiments, the cancer is a liver cancer. In some embodiments, the cancer is a thyroid cancer. In some embodiments, the cancer is CLL.

In some embodiments, the ER-α36 positive cancer is also an EGFR positive cancer, for example, an EGFR positive breast cancer or an EGFR positive lung cancer. Where the ER-α36 positive cancer is also EGFR positive, the method may further comprise administering to the individual an EGFR kinase inhibitor. In some embodiments, lasofoxifene or pharmaceutically acceptable salt thereof and the EGFR kinase inhibitor are administered simultaneously. In some embodiments, lasofoxifene or pharmaceutically acceptable salt thereof and the EGFR kinase inhibitor are administered sequentially. Any EGFR kinase inhibitor may be co-administered with lasofoxifene or pharmaceutically acceptable salt thereof, such as, including but not limited to, gefitinib, erlotinib, icotinib, afatinib, neratinib, dacomitinib, osimertinib, rociletinib orolmutinib, or a pharmaceutically acceptable salt thereof.

In some embodiments, the ER-α36 positive cancer is also a HER2 positive cancer, for example, a HER2 positive breast cancer or a HER2 positive gastric cancer. Where the ER-α36 positive cancer is also HER2 positive, the method may further comprise administering to the individual an HER2 inhibitor. In some embodiments, lasofoxifene or pharmaceutically acceptable salt thereof and the HER2 inhibitor are administered simultaneously. In some embodiments, lasofoxifene or pharmaceutically acceptable salt thereof and the HER2 inhibitor are administered sequentially. Any HER2 inhibitor may be co-administered with lasofoxifene or pharmaceutically acceptable salt thereof, such as, including but not limited to, trastuzumab, pertuzumab, lapatinib or ado-trastuzumab emtansine (T-DM1). In some embodiments, the HER2 inhibitor is an anti-HER2 antibody.

Also provided is a method of treating an ER-α36 positive cancer in an individual comprising administering to the individual: a) an effective amount of lasofoxifene or a pharmaceutically acceptable salt thereof; and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the EGFR phosphorylation inhibitor is gefitinib or a pharmaceutically acceptable salt thereof. In some embodiments, the HER2 inhibitor is trastuzumab (e.g.) Herceptin®.

In some embodiments, the method of treating cancer (e.g., an ER-α 36 positive and EGFR positive cancer) comprises administering to an individual in need thereof an effective amount of lasofoxifene or a pharmaceutically acceptable salt thereof and an effective amount of an EGFR kinase inhibitor (e.g., gefitinib, erlotinib, icotinib, afatinib, neratinib, dacomitinib, osimertinib, rociletinib or olmutinib, or a pharmaceutically acceptable salt thereof) or a functional equivalent thereof. In some embodiments, the method of treating cancer (e.g., an ER-α 36 positive and EGFR positive cancer) comprises administering to an individual in need thereof an effective amount of lasofoxifene or a pharmaceutically acceptable salt thereof and an effective amount of gefitinib or a pharmaceutically acceptable salt thereof.

In some embodiments, the method of treating cancer (e.g., an ER-α 36 positive and HER2 positive cancer) comprises administering to an individual in need thereof an effective amount of lasofoxifene or a pharmaceutically acceptable salt thereof and an effective amount of a HER2 inhibitor (e.g., trastuzumab, pertuzumab, lapatinib, or ado-trastuzumab emtansine (T-DM1), or a pharmaceutically acceptable salt thereof) or a functional equivalent thereof. In some embodiments, the method of treating cancer (e.g., an ER-α 36 positive and HER2 positive cancer) comprises administering to an individual in need thereof an effective amount of lasofoxifene or a pharmaceutically acceptable salt thereof and an effective amount of trastuzumab (e.g.) Herceptin®.

In some embodiments, lasofoxifene or a pharmaceutically acceptable salt thereof and the other agent (such as an EGFR kinase inhibitor or functional equivalent detailed herein or a HER2 inhibitor or functional equivalent detailed herein) are administered sequentially. In some embodiments, lasofoxifene or a pharmaceutically acceptable salt thereof and the other agent (such as an EGFR kinase inhibitor or functional equivalent detailed herein or a HER2 inhibitor or functional equivalent detailed herein) are administered simultaneously.

In some embodiments, lasofoxifene or a pharmaceutically acceptable salt thereof and the other agent (e.g., an EGFR kinase inhibitor or functional equivalent detailed herein or a HER2 inhibitor or functional equivalent detailed herein) are administered concurrently. For example, in some embodiments, the administrations of lasofoxifene or a pharmaceutically acceptable salt thereof and the other agent are initiated at about the same time (for example, within any one of 1, 2, 3, 4, 5, 6, or 7 days). In some embodiments, the administrations of lasofoxifene or a pharmaceutically acceptable salt thereof and the other agent are terminated at about the same time (for example, within any one of 1, 2, 3, 4, 5, 6, or 7 days). In some embodiments, the administration of the other agent continues (for example for about any one of 0.5, 1, 2, 3, 4, 5, 6, 7, 8, 9, 10, 11, or 12 months) after the termination of the administration of lasofoxifene or a pharmaceutically acceptable salt thereof. In some embodiments, the administration of the other agent is initiated after (for example after about any one of 0.5, 1, 2, 3, 4, 5, 6, 7, 8, 9, 10, 11, or 12 months) the initiation of the administration of lasofoxifene or a pharmaceutically acceptable salt thereof. In some embodiments, the administrations of lasofoxifene or a pharmaceutically acceptable salt thereof and the other agent are initiated and terminated at about the same time.

In some embodiments, the administrations of lasofoxifene or a pharmaceutically acceptable salt thereof and the other agent (e.g., an EGFR kinase inhibitor or functional equivalent detailed herein or a HER2 inhibitor or functional equivalent detailed herein) are initiated at about the same time and the administration of the other agent continues (for example for about any one of 0.5, 1, 2, 3, 4, 5, 6, 7, 8, 9, 10, 11, or 12 months) after the termination of the administration of lasofoxifene or a pharmaceutically acceptable salt thereof. In some embodiments, the administration of lasofoxifene or a pharmaceutically acceptable salt thereof and the other agent stop at about the same time and the administration of the other agent is initiated after (for example after about any one of 0.5, 1, 2, 3, 4, 5, 6, 7, 8, 9, 10, 11, or 12 months) the initiation of the administration of lasofoxifene or a pharmaceutically acceptable salt thereof. In some embodiments, the administration of lasofoxifene or a pharmaceutically acceptable salt thereof and the other agent stop at about the same time and the administration of lasofoxifene or a pharmaceutically acceptable salt thereof is initiated after (for example after about any one of 0.5, 1, 2, 3, 4, 5, 6, 7, 8, 9, 10, 11, or 12 months) the initiation of the administration of the other agent.

The other agents described herein (such as an EGFR kinase inhibitor or functional equivalent detailed herein or a HER2 inhibitor or functional equivalent detailed herein) can be the agents themselves, pharmaceutically acceptable salts thereof, and pharmaceutically acceptable esters thereof, as well as stereoisomer, enantiomers, racemic mixtures, and the like. The other agent or agents as described can be administered as well as a pharmaceutical composition containing the agent(s), wherein the pharmaceutical composition comprises a pharmaceutically acceptable carrier vehicle, or the like.

The methods described herein require administration of lasofoxifene or a pharmaceutically acceptable salt thereof and the other agent, where present, in effective amounts. In some embodiments, an effective amount is an amount sufficient to delay development of cancer. In some embodiments, an effective amount is an amount sufficient to prevent or delay recurrence. An effective amount can be administered in one or more administrations. In some embodiments, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay recurrence of tumor; and/or (vii) relieve to some extent one or more of the symptoms associated with the cancer.

Thus, in some embodiments, there is provided a method of inhibiting cell proliferation (such as tumor growth) in an individual, comprising administering to the individual: a) an effective amount lasofoxifene or a pharmaceutically acceptable salt thereof, and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the effective amounts of lasofoxifene or a pharmaceutically acceptable salt thereof and the other agent synergistically inhibit cell proliferation (such as tumor cell growth). In some embodiments, at least about 10% (including for example at least about any of 20%, 30%, 40%, 60%, 70%, 80%, 90%, or 100%) cell proliferation is inhibited. In some embodiments, the individual (e.g., human) is ER-α36 positive.

In some embodiments, there is provided a method of inhibiting tumor metastasis (such as metastasis of breast cancer, pulmonary metastasis or metastasis to the lymph node) in an individual, comprising administering to the individual: a) an effective amount lasofoxifene, and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the effective amounts of lasofoxifene and the other agent synergistically inhibit tumor metastasis. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided. In some embodiments, method of inhibiting metastasis to the lung is provided. In some embodiments, the individual (e.g., human) is ER-α36 positive.

In some embodiments, there is provided a method of reducing incidence or burden of preexisting tumor metastasis (such as pulmonary metastasis or metastasis to the lymph node) in an individual, comprising administering to the individual: a) an effective amount lasofoxifene, and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the individual (e.g., human) is ER-α36 positive.

In some embodiments, there is provided a method of reducing tumor size in an individual, comprising administering to the individual: a) an effective amount lasofoxifene, and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the tumor size is reduced at least about 10% (including for example at least about any of 20%, 30%, 40%, 60%, 70%, 80%, 90%, or 100%). In some embodiments, the individual (e.g., human) is ER-α36 positive.

In some embodiments, there is provided a method of prolonging time to disease progression of a cancer in an individual, comprising administering to the individual: a) an effective amount lasofoxifene, and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the method prolongs the time to disease progression by at least any of 1, 2, 3, 4, 5, 6, 7, 8, 9, 10, 11, or 12 weeks. In some embodiments, the individual (e.g., human) is ER-α36 positive.

In some embodiments, there is provided a method of prolonging survival of an individual having a proliferative disease (such as an ER-α36 positive cancer), comprising administering to the individual: a) an effective amount lasofoxifene, and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof. In some embodiments, the method prolongs the survival of the individual by at least any of 1, 2, 3, 4, 5, 6, 7, 8, 9, 10, 11, 12, 18, or 24 month.

In some embodiments, the method is used to treat a primary tumor (e.g., an ER-α36 positive tumor). In some embodiments, a method of treating metastatic cancer (that is, cancer that has metastasized from the primary tumor) (e.g., an ER-α36 positive metastatic cancer) is provided. In some embodiments, the method is for the treatment of an advanced disease or a lesser extent of disease, such as low tumor burden. In some embodiments, there is provided a method of treating cancer (e.g., an ER-α36 positive cancer) at an advanced stage. In some embodiments, the method is for the treatment of an early stage breast cancer. The methods may be practiced in an adjuvant setting. The methods provided herein may also be practiced in a neoadjuvant setting, i.e., the method may be carried out before the primary/definitive therapy. In some embodiments, the method further comprises conducting surgery on the individual following the completion of the treatment. For example, in some embodiments when the cancer is breast cancer (e.g., an ER-α36 positive breast cancer), breast conserving surgery or mastectomy can be carried out within about 2, 3, 4, 5, 6, 7, 8, 9, 10, 11, or 12 weeks after completion of the neoadjuvant chemotherapy.

In some embodiments, the individual has previously been treated. In some embodiments, the individual has not previously been treated. In some embodiments, the treatment is a first line therapy. In some embodiments, the breast cancer (e.g., an ER-α36 positive breast cancer) has reoccurred after a remission.

In some embodiments, the cancer is breast cancer. These methods can be used, for example, to treat, stabilize, and/or delay any type or stage of breast cancer, such as early stage breast cancer, non-metastatic breast cancer, advanced breast cancer, stage IV breast cancer, locally advanced breast cancer, metastatic breast cancer, breast cancer in remission, breast cancer in an adjuvant setting, or breast cancer in a neoadjuvant setting. In some embodiments, the method is useful for preoperative systemic therapy (PST). In some embodiments, the breast cancer is an ER-α36 positive breast cancer.

In some embodiments, there is provided a method of treating breast cancer (which may be HER2 positive or HER2 negative), including, for example, advanced breast cancer, stage IV breast cancer, locally advanced breast cancer, and metastatic breast cancer. In some embodiments, the breast cancer is luminal type B breast cancer. In some embodiments, the breast cancer is basal cell breast cancer. In some embodiments, the individual is diagnosed with T2, T3, or T4 lesion, or a stage N, M0 or T1c, N1-3 and M0. In some embodiments, the individual has an ECOG performance status of 0-1. In some embodiments, the individual has skin metastasis to the ipsilateral breast. In some embodiments, the individual has undergone prior therapy (such as hormonal therapy). In some embodiments, the individual has not undergone prior therapy (such as hormonal therapy). In some embodiments, the individual is awaiting definitive surgery. In some embodiments, the breast cancer is resected breast cancer. In some embodiments, the breast cancer is unresected breast cancer, such as unresected stage II or III breast cancer. In some embodiments, the breast cancer is an ER-α36 positive breast cancer.

In some embodiments, the method is for treating an individual having one or more of these risk factors resulting in a higher probability of developing breast cancer than an individual without these risk factor(s). These risk factors include, but are not limited to, age, sex, race, diet, history of previous disease, presence of precursor disease, genetic (i.e., hereditary) considerations, and environmental exposure. In some embodiments, the individual may be a human who is genetically or otherwise predisposed to developing breast cancer who has or has not been diagnosed with breast cancer. Individuals at risk for breast cancer include, e.g., those having relatives who have experienced this disease, and those whose risk is determined by analysis of genetic or biochemical markers. For example, the individual may be a human who has a gene, genetic mutation, or polymorphism associated with breast cancer (e.g., BRCA1, BRCA2, ATM, CHEK2, RAD51, AR, DIRAS3, ERBB2, and/or TP53) or has one or more extra copies of a gene (e.g., one or more extra copies of the HER2 gene) associated with breast cancer. In some embodiments, the breast cancer is HER2 negative. In some embodiments, the breast cancer is ER negative. In some embodiments, the breast cancer is PR negative. In some embodiments, the breast cancer is ER negative and HER2 negative. In some embodiments, the breast cancer is PR negative and HER2 negative. In some embodiments, the breast cancer is ER negative and PR negative. In some embodiment, the breast cancer is ER negative, PR negative, and HER2 negative.

The methods described herein are also useful for treating other solid tumors (such as advanced solid tumors). In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, uterine endometrial cancer, head and neck cancer, gastric malignancies, melanoma (including metastatic melanoma and malignant melanoma), ovarian cancer, colorectal cancer, and pancreatic cancer. In some embodiments, the cancer detailed above is ER-α36 positive.

In some embodiments, the method is useful for treating one or more of the following: cutaneous T cell lymphoma (CTCL), leukemia, follicular lymphoma, Hodgkin lymphoma, and acute myeloid leukemia. In some embodiments, the cancer detailed above is ER-α36 positive.

In some embodiments, the cancer is any one of the following: basal cell carcinoma, medulloblastoma, glioblastoma, multiple myeloma, chronic myelogenous leukemia (CIVIL), acute myelogenous leukemia, pancreatic cancer, lung cancer (small cell lung cancer and non-small cell lung cancer), esophageal cancer, stomach cancer, biliary cancer, prostate cancer, liver cancer, hepatocellular cancer, gastrointestinal cancer, gastric cancer, thyroid cancer, uterine endometrial cancer and ovarian and bladder cancer. In some embodiments, the cancer is selected from the group consisting of pancreas ductal adenocarcinoma, colon adenocarcinoma, uterine endometrial cancer, and ovary cystadenocarcinoma. In some embodiments, the cancer is pancreas ductal adenocarcinoma. In some embodiments, the cancer is a tumor that is poorly perfused and/or poorly vascularized. In some embodiments, the cancer detailed above is ER-α36 positive.

In some embodiments, the cancer is pancreatic cancer, including for example pancreatic adenocarcinoma, pancreatic adenosquamous carcinoma, pancreatic squamous cell carcinoma, and pancreatic giant cell carcinoma. In some embodiments, the pancreatic cancer is exocrine pancreatic cancer. In some embodiments, the pancreatic cancer is endocrine pancreatic cancer (such as islet cell carcinoma). In some embodiments, the pancreatic cancer is advanced metastatic pancreatic cancer. In some embodiments, the pancreatic cancer detailed above is an ER-α36 positive pancreatic cancer.

Other examples of cancers that may be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the cancer is a solid tumor (such as advanced solid tumor). Solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, uterine endometrial cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (including for example adenocarcinoma, clear cell renal cell carcinoma, papillary renal cell carcinoma, chromophobe renal cell carcinoma, collecting duct renal cell carcinoma, granular renal cell carcinoma, mixed granular renal cell carcinoma, renal angiomyolipomas, or spindle renal cell carcinoma), hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. In some embodiments, the cancer detailed above is ER-α36 positive.

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type+/−monocytoid B cells) and/or Nodal (e.g., +/−monocytoid B cells)), splenic marginal zone lymphoma (e.g., +/−villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia). In some embodiments, the lymphoid neoplasm detailed above is ER-α36 positive.

In some embodiments the lymphoid neoplasm (e.g., lymphoma) is a T-cell and/or putative NK-cell neoplasm. Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/− enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's like). In some embodiments, the lymphoid neoplasm detailed above is ER-α36 positive.

In some embodiments the lymphoid neoplasm (e.g., lymphoma) is Hodgkin's disease (e.g., an ER-α36 positive Hodgkin's disease). For example, the Hodgkin's disease may be lymphocyte predominance, nodular sclerosis, mixed cellularity, lymphocyte depletion, and/or lymphocyte-rich.

In some embodiments, the cancer is leukemia (e.g., an ER-α36 positive leukemia). In some embodiments, the leukemia is chronic leukemia. Examples of chronic leukemia include, but are not limited to, chronic myelocytic I (granulocytic) leukemia, chronic myelogenous, and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, the cancer is multiple myeloma (e.g., an ER-α36 positive multiple myeloma). Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex-), doxorubicin (Dox-), and melphalan (LR).

In some embodiments, there are provided methods of reducing side effect of at least one other agent by lasofoxifene or a pharmaceutically acceptable salt thereof, comprising administering to the individual an effective amount of lasofoxifene or a pharmaceutically acceptable salt thereof in combination with the other agent, wherein the other agent is selected from the group consisting of tamoxifen, raloxifene or functional equivalent thereof, and an aromatase inhibitor. In some embodiments, the individual is ER-α36 positive. In some embodiments, the individual is EGFR positive. In some embodiments, the individual is HER2 positive.

In some embodiments, the cancer is selected from the group consisting of breast cancer, uterine endometrial cancer, lung cancer, pancreatic cancer, gastric cancer, colon cancer, liver cancer, thyroid cancer, CLL, and the like, whose cells positively express ER-α36. In some embodiments, the ER-α36 positive breast cancer is resistant to treatment with tamoxifen.

In some aspects of the method of treating an ER-α36 positive cancer may further comprise determining ER-α36 expression in the cancer, for example, by the presence of an ER-α36 peptide and/or the presence of ER-α36 mRNA. In some embodiments, ER-α36 expression in the cancer is determined by presence of an ER-α36 peptide, for example, as measured by an immuno-hybridization method (e.g., western blotting, immuno-histological or -fluorescence staining). In some embodiments, ER-α36 expression in the cancer is determined by presence of an ER-α36 mRNA, for example, as measured by quantitative polymerase chain reaction (q-PCR).

In some embodiments, ER-α36 status is used as a basis for selecting individuals for cancer treatment (or reducing side effects of the other agents in cancer treatment). The levels of ER-α36 can be used, for example, for determining (and aiding assessment) in any one or more of the following: a) probably or likely suitability of an individual to initially receive treatment; b) probable or likely unsuitability of an individual to initially receive treatment(s); c) responsiveness to treatment; d) probable or likely suitability of an individual to continue to receive treatment; e) probable or likely unsuitability of an individual to receive treatment(s); f)

adjusting dosages; g) predicting likelihood of clinical benefits. The present application encompasses any of these methods.

For example, in some embodiments, there is provided a method of treating cancer in an individual (such as a human individual) comprising administering to the individual: a) an effective amount of lasofoxifene or a pharmaceutically acceptable salt thereof; and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof, wherein the individual is ER-α36 positive (for example, the individual has a high level of ER-α36). In some embodiments, there is provided a method of treating cancer in an individual (such as a human individual) comprising administering to the individual: a) an effective amount of lasofoxifene or a pharmaceutically acceptable salt thereof; and optionally b) an effective amount of at least one other agent selected from the group consisting of a phosphorylation kinase inhibitor of epithelia growth factor receptor such as EGFR phosphorylation inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof, and an inhibitor of HER2 (e.g., trastuzumab, pertuzumab, lapatinib, or ado-trastuzumab emtansine (T-DM1), or a pharmaceutically acceptable salt thereof) or a functional equivalent thereof, wherein the level of ER-α36 is used as a basis for selecting the individual for treatment. In some embodiments, the individual is selected for treatment if the individual has a high level of ER-α36. In some embodiments, the level of ER-α36 is determined by immunohistochemistry method. In some embodiments, the level of the ER-α36 is based on protein expression level. In some embodiments, the level of the ER-α36 is based on mRNA level. In some embodiments, the level of the ER-α36 is based on $Ca^{2+}$ signal in response to estrogen stimulation. In some embodiments, the method further comprises determining the level of the ER-α36 prior to the treatment. In some embodiments, the method further comprises selecting the individual for treatment based on the ER-α36 level.

The levels of ER-α36 may be a high level or a low level as compared to a control sample. In some embodiments, the level of the ER-α36 in an individual is compared to the level of the ER-α36 in a control sample. In some embodiments the level of the ER-α36 in a subject is compared to the level of the ER-α36 in multiple control samples. In some embodiments, multiple control samples are used to generate a statistics that is used to classify the level of the ER-α36 in an individual with cancer.

The classification or ranking of the ER-α36 level (i.e., high or low) may be determined relative to a statistical distribution of control levels. In some embodiments, the classification or ranking is relative to a control sample obtained from the individual. In some embodiment the levels of the ER-α36 is classified or ranked relative to a statistical distribution of control levels. In some embodiments, the level of the ER-α36 is classified or ranked relative to the level from a control sample obtained from the subject.

Control samples can be obtained using the same sources and methods as non-control samples. In some embodiments, the control sample is obtained from a different individual (for example an individual not having cancer and/or an individual sharing similar ethnic, age, and gender identity). In some embodiments when the sample is a tumor tissue sample, the control sample may be a non-cancerous sample from the same individual. In some embodiments, multiple control samples (for example from different individuals) are used to determine a range of levels of ER-α36 in a particular tissue, organ, or cell population. In some embodiments, the control sample is a cultured tissue or cell that has been determined to be a proper control. In some embodiments, the control is a cell that does not express the ER-α36. In some embodiments, a clinically accepted normal level in a standardized test is used as a control level for determining the ER-α36 level. In some embodiments, the reference level of ER-α36 in the subject is classified as high, medium or low according to a scoring system, such as an immunohistochemistry-based scoring system.

In some embodiments, the ER-α36 level is determined by measuring the level of a ER-α36 in an individual and comparing to a control or reference (e.g., the median level for the given patient population or level of a second individual). For example, if the level of ER-α36 for the single individual is determined to be above the median level of the patient population, that individual is determined to have high expression of the ER-α36. Alternatively, if the level of a ER-α36 for the single individual is determined to be below the median level of the patient population, that individual is determined to have low expression of the ER-α36. In some embodiments, the individual is compared to a second individual and/or a patient population which is responsive to treatment. In some embodiments, the individual is compared to a second individual and/or a patient population which is not responsive to treatment. In any of the embodiments herein, the levels are determined by measuring the level of ER-α36. For example, if the level of an mRNA encoding ER-α36 for the single individual is determined to be above the median level of the patient population, that individual is determined to have a high level of an mRNA encoding ER-α36. Alternatively, if the level of mRNA encoding the ER-α36 for the single individual is determined to be below the median level of the patient population, that individual is determined to have a low level of an mRNA encoding ER-α36.

In some embodiments, the reference level of ER-α36 is determined by obtaining a statistical distribution of ER-α36 levels.

In some embodiments, bioinformatics methods are used for the determination and classification of the levels of ER-α36. Numerous alternative bioinformatics approaches have been developed to assess gene set expression profiles using gene expression profiling data. Methods include but are not limited to those described in Segal, E. et al. Nat. Genet. 34:66-176 (2003); Segal, E. et al. Nat. Genet. 36:1090-1098 (2004); Barry, W. T. et al. Bioinformatics 21:1943-1949 (2005); Tian, L. et al. Proc Nat'l Acad Sci USA 102:13544-13549 (2005); Novak B A and Jain A N. Bioinformatics 22:233-41 (2006); Maglietta R et al. Bioinformatics 23:2063-72 (2007); Bussemaker H J, BMC Bioinformatics 8 Suppl 6:S6 (2007).

In some embodiments, mRNA level is determined, and a low level is an mRNA level that is less than about 2, 1.9, 1.8, 1.7, 1.6 or 1.5 times of the level considered as clinically normal or of the level obtained from a control. In some embodiments, high level is an mRNA level more than about 2, 2.2, 2.5, 2.7, 3, 5, 7, 10, 20, 50, 70, 100, 200, 500, 1000 times or more than 1000 times of that considered as clinically normal or of the level obtained from a control sample.

In some embodiments, protein expression level is determined, for example by immunohistochemistry. For example, the criteria for low or high levels can be made based on the number of positive staining cells and/or the intensity of the staining, for example by using an antibody that specifically recognizes the ER-α36 protein. In some embodiments, the level is low if less than about 1%, 5%, 10%, 15%, 20%, 25%, 30%, 35%, 40%, 45%, or 50% cells have positive staining. In some embodiments, the level is low if the staining is 1%, 5%, 10%, 15%, 20%, 25%, 30%, 35%, 40%, 45%, or 50% less intense than a positive control staining. In some embodiments, a positive control staining for tumor cells has an intensity that is about twice that of normal cells.

In some embodiments, the level is high if more than about 40%, 45%, 50%, 55%, 60%, 65%, 70%, 75%, 80%, 85%, or 90%, cells have positive staining. In some embodiments, the level is high if the staining is as intense as positive control staining. In some embodiments, the level is high if the staining is 80%, 85%, or 90% as intense as positive control staining. In some embodiments, a positive control staining for tumor cells has an intensity that is about twice that of normal cells.

In some embodiments, strong staining, moderate staining, and weak staining are calibrated levels of staining, wherein a range is established and the intensity of staining is binned within the range. In some embodiments, strong staining is staining above the 75th percentile of the intensity range, moderate staining is staining from the 25th to the 75th percentile of the intensity range, and low staining is staining is staining below the 25th percentile of the intensity range. In some aspects one skilled in the art, and familiar with a particular staining technique, adjusts the bin size and defines the staining categories.

In some embodiments, estrogen sensitivity level is determined, for example by $Ca^{2+}$ oscillation or electrophysiological patch clamp. For example, the criteria for low or high levels can be made based on the change of $Ca^{2+}$ concentration or responsive signal of positive cells, for example by using estrogen. In some embodiments, the level is low if less than about 1%, 5%, 10%, 15%, 20%, 25%, 30%, 35%, 40%, 45%, or 50% cells have positive sensitivity. In some embodiments, the level is low if the change of $Ca^{2+}$ concentration or responsive signal is 1%, 5%, 10%, 15%, 20%, 25%, 30%, 35%, 40%, 45%, or 50% less intense than a positive control sensitivity. In some embodiments, positive control sensitivity in tumor cells is about twice that of normal cells.

In some embodiments, the level is high if more than about 40%, 45%, 50%, 55%, 60%, 65%, 70%, 75%, 80%, 85%, or 90%, cells have positive change. In some embodiments, the level is high if the sensitivity is as intense as positive control sensitivity. In some embodiments, the level is high if the change is 80%, 85%, or 90% as intense as positive control. In some embodiments, positive control sensitivity in tumor cells is about twice that of normal cells.

In some embodiments, most sensitivity, moderate sensitivity, and weak sensitivity are calibrated levels of $Ca^{2+}$ signal in cells, wherein a range is established and the intensity of $Ca^{2+}$ signal is binned within the range. In some embodiments, most sensitivity is the change of $Ca^{2+}$ signal above the 75th percentile of the intensity range, moderate sensitivity is the change of $Ca^{2+}$ signal from the 25th to the 75th percentile of the intensity range, and low sensitivity is the change of $Ca^{2+}$ signal is measuring below the 25th percentile of the intensity range. In some aspects one skilled in the art, and familiar with a particular perfusion technique, adjusts the bin size and defines the signal recording categories.

Also provided is lasofoxifene, or a pharmaceutically acceptable salt thereof, for use in a method for the treatment of an ER-α36 positive cancer, such as an ER-α36 positive cancer detailed herein. In some embodiments, provided is a combination of lasofoxifene, or a pharmaceutically acceptable salt thereof, with another agent selected from the group consisting of tamoxifen or functional equivalent thereof, an EGFR kinase inhibitor (e.g., gefitinib) or a functional equivalent thereof, and a HER2 inhibitor (e.g., trastuzumab) or a functional equivalent thereof, for the treatment of an ER-α36 positive cancer, wherein the cancer also expresses a biomarker such as an EGFR kinase or HER2.

Further provided is a use of lasofoxifene, or a pharmaceutically acceptable salt thereof, in the manufacture of a medicament for the treatment of an ER-α36 positive cancer, such as an ER-α36 positive cancer detailed herein. In some embodiments, provided is a use of a combination of lasofoxifene, or a pharmaceutically acceptable salt thereof, with another agent selected from the group consisting of tamoxifen or functional equivalent thereof, an EGFR kinase inhibitor (e.g., gefitinib, erlotinib, icotinib, afatinib, neratinib, dacomitinib, osimertinib, rociletinib or olmutinib, or a pharmaceutically acceptable salt thereof) or a functional equivalent thereof, and a HER2 inhibitor (e.g., trastuzumab, pertuzumab, lapatinib, or ado-trastuzumab emtansine (T-DM1), or a pharmaceutically acceptable salt thereof) or a functional equivalent thereof, in the manufacture of a medicament for the treatment of an ER-α36 positive cancer, wherein the cancer also expresses a biomarker such as an EGFR kinase or HER2.

In some embodiments of the methods detailed herein for treating an ER-α36 positive cancer, the method comprises administering to the individual an effective amount of lasofoxifene. In some embodiments, the individual is a human (e.g., an ER-α36 positive human).

Modes of Administration

In the context of combination therapy, the composition comprising lasofoxifene or a pharmaceutically acceptable salt thereof and the other agent (e.g., an EGFR kinase inhibitor or functional equivalent detailed herein or a HER2 inhibitor or functional equivalent detailed herein) can be administered simultaneously (i.e., simultaneous administration) and/or sequentially (i.e., sequential administration). In some embodiments, lasofoxifene or a pharmaceutically acceptable salt thereof and the other agent (including the specific agents described herein) are administered simultaneously. The term "simultaneous administration," as used herein, means that lasofoxifene or a pharmaceutically acceptable salt thereof and the other agent are administered with a time separation of no more than about 15 minute(s), such as no more than about any of 10, 5, or 1 minutes. When the drugs are administered simultaneously, lasofoxifene or a pharmaceutically acceptable salt thereof and the other agent may be contained in the same composition (e.g., a composition comprising both lasofoxifene or a pharmaceutically acceptable salt thereof and the other agent, for example the pharmaceutical composition comprised herein) or in separate compositions (e.g., lasofoxifene or a pharmaceutically acceptable salt thereof and the other agent are contained in separate compositions).

In some embodiments, lasofoxifene or a pharmaceutically acceptable salt thereof and the other agent (e.g., an EGFR kinase inhibitor or functional equivalent detailed herein or a HER2 inhibitor or functional equivalent detailed herein) are administered sequentially. The term "sequential administration" as used herein means that lasofoxifene or a pharmaceutically acceptable salt thereof and the other agent are administered with a time separation of more than about 15 minutes, such as more than about any of 20, 30, 40, 50, 60 or more minutes. Either lasofoxifene or a pharmaceutically acceptable salt thereof or the other agent may be administered first. Lasofoxifene or a pharmaceutically acceptable salt thereof and the other agent are contained in separate compositions, which may be contained in the same or different packages.

In some embodiments, the administration of lasofoxifene or a pharmaceutically acceptable salt thereof and the other agent (e.g., an EGFR kinase inhibitor or functional equivalent detailed herein or a HER2 inhibitor or functional equivalent detailed herein) are concurrent, i.e., the administration period of lasofoxifene or a pharmaceutically acceptable salt thereof and that of the other agent overlap with each other. In some embodiments, lasofoxifene or a pharmaceutically acceptable salt thereof is administered for at least one cycle (for example, at least any of 2, 3, or 4 cycles) prior to the administration of the other agent. In some embodiments, the other agent is administered for at least any of one, two, three, or four weeks. In some embodiments, the administrations of lasofoxifene or a pharmaceutically acceptable salt thereof and the other agent are initiated at about the same time (for example, within any one of 1, 2, 3, 4, 5, 6, or 7 days). In some embodiments, the administrations of lasofoxifene or a pharmaceutically acceptable salt thereof and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of lasofoxifene or a pharmaceutically acceptable salt thereof. In some embodiments, the administration of the other agent is initiated after (for example after about any one of 1, 2, 3, 4, 5, 6, 7, 8, 9, 10, 11, or we months) the initiation of the administration of lasofoxifene or a pharmaceutically acceptable salt thereof. In some embodiments, the administrations of lasofoxifene or a pharmaceutically acceptable salt thereof and the other agent are initiated and terminated at about the same time. In some embodiments, the administrations of lasofoxifene or a pharmaceutically acceptable salt thereof and the other agent are initiated at about the same time and the administration of the other agent continues (for example for about any one of 1, 2, 3, 4, 5, 6, 7, 8, 9, 10, 11, or 12 months) after the termination of the administration of lasofoxifene or a pharmaceutically acceptable salt thereof. In some embodiments, the administration of lasofoxifene or a pharmaceutically acceptable salt thereof and the other agent stop at about the same time and the administration of the other agent is initiated after (for example after about any one of 1, 2, 3, 4, 5, 6, 7, 8, 9, 10, 11, or we months) the initiation of the administration of lasofoxifene or a pharmaceutically acceptable salt thereof.

The dosing frequency of lasofoxifene or a pharmaceutically acceptable salt thereof and/or the other agent (e.g., an EGFR kinase inhibitor or functional equivalent detailed herein or a HER2 inhibitor or functional equivalent detailed herein) may be adjusted over the course of the treatment, based on the judgment of the administering physician. When administered separately, lasofoxifene or a pharmaceutically acceptable salt thereof and the other agent can be administered at different dosing frequency or intervals. For example, lasofoxifene or a pharmaceutically acceptable salt thereof can be administered weekly, while another agent can be administered more or less frequently. Various formulations and devices for achieving sustained release are known in the art. Exemplary dosing frequencies are further provided herein.

Lasofoxifene or a pharmaceutically acceptable salt thereof and the other agent (e.g., an EGFR kinase inhibitor or functional equivalent detailed herein or a HER2 inhibitor or functional equivalent detailed herein) can be administered using the same route of administration or different routes of administration. Exemplary administration routes are further provided herein. In some embodiments (for both simultaneous and sequential administrations), lasofoxifene or a pharmaceutically acceptable salt thereof and the other agent are administered at a predetermined ratio. For example, in some embodiments, the ratio by weight of lasofoxifene or a pharmaceutically acceptable salt thereof and the other agent is about 1 to 1. In some embodiments, the weight ratio may be between about 0.001 to about 1 and about 1000 to about 1, or between about 0.01 to about 1 and 100 to about 1. In some embodiments, the ratio by weight of lasofoxifene or a pharmaceutically acceptable salt thereof and the other agent is less than about any of 100:1, 50:1, 30:1, 10:1, 9:1, 8:1, 7:1, 6:1, 5:1, 4:1, 3:1, 2:1, and 1:1 In some embodiments, the ratio by weight of lasofoxifene or a pharmaceutically acceptable salt thereof and the other agent is more than about any of 1:1, 2:1, 3:1, 4:1, 5:1, 6:1, 7:1, 8:1, 9:1, 30:1, 50:1, 100:1. Other ratios are contemplated.

The doses required for lasofoxifene or a pharmaceutically acceptable salt thereof and/or the other agent (e.g., an EGFR kinase inhibitor or functional equivalent detailed herein or a HER2 inhibitor or functional equivalent detailed herein) may (but not necessarily) be lower than what is normally required when each agent is administered alone. Thus, in some embodiments, a subtherapeutic amount of the drug in lasofoxifene or a pharmaceutically acceptable salt thereof and/or the other agent are administered. "Subtherapeutic amount" or "subtherapeutic level" refer to an amount that is less than therapeutic amount, that is, less than the amount normally used when the drug in lasofoxifene or a pharmaceutically acceptable salt thereof and/or the other agent are administered alone. The reduction may be reflected in terms of the amount administered at a given administration and/or the amount administered over a given period of time (reduced frequency).

In some embodiments, enough other agent (e.g., an EGFR kinase inhibitor or functional equivalent detailed herein or a HER2 inhibitor or functional equivalent detailed herein) is administered so as to allow reduction of the normal dose of lasofoxifene or a pharmaceutically acceptable salt thereof required to effect the same degree of treatment by at least about any of 5%, 10%, 20%, 30%, 50%, 60%, 70%, 80%, 90%, or more. In some embodiments, enough lasofoxifene or a pharmaceutically acceptable salt thereof is administered so as to allow reduction of the normal dose of the other agent required to effect the same degree of treatment by at least about any of 5%, 10%, 20%, 30%, 50%, 60%, 70%, 80%, 90%, or more.

In some embodiments, the doses of both lasofoxifene or a pharmaceutically acceptable salt thereof and the other agent (e.g., an EGFR kinase inhibitor or functional equivalent detailed herein or a HER2 inhibitor or functional equivalent detailed herein) are reduced as compared to the corresponding normal dose of each when administered alone. In some embodiments, both lasofoxifene or a pharmaceutically acceptable salt thereof and the other agent are administered at a subtherapeutic, i.e., reduced, level. In some embodiments, the dose of lasofoxifene or a pharmaceutically acceptable salt thereof and/or the other agent is substantially less than the established maximum toxic dose (MTD). For example, the dose of lasofoxifene or a pharmaceutically acceptable salt thereof and/or the other agent is less than about 50%, 40%, 30%, 20%, or 10% of the MTD.

In some embodiments, the dose of lasofoxifene or a pharmaceutically acceptable salt thereof and/or the dose of the other agent (e.g., an EGFR kinase inhibitor or functional equivalent detailed herein or a HER2 inhibitor or functional equivalent detailed herein) is higher than what is normally required when each agent is administered alone. For example, in some embodiments, the dose of lasofoxifene or a pharmaceutically acceptable salt thereof and/or the other agent is substantially higher than the MTD. For example, the dose of lasofoxifene or a pharmaceutically acceptable salt thereof and/or the other agent is more than about 50%, 40%, 30%, 20%, or 10% of the MTD of the agent when administered alone.

In some embodiments, the amount of lasofoxifene or a pharmaceutically acceptable salt thereof (alone or in combination with another agent (e.g., an EGFR kinase inhibitor or functional equivalent detailed herein or a HER2 inhibitor or functional equivalent detailed herein)) is included in any of the following ranges: about 0.1 to about 0.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of lasofoxifene or a pharmaceutically acceptable salt thereof (e.g., a unit dosage form) is in the range of about 5 mg to about 500 mg, such as about 30 mg to about 300 mg or about 50 mg to about 200 mg.

In some embodiments, the amount of lasofoxifene or a pharmaceutically acceptable salt thereof (alone or in combination with another agent (e.g., an EGFR kinase inhibitor or functional equivalent detailed herein or a HER2 inhibitor or functional equivalent detailed herein)) includes at least about any of 0.01 mg/kg, 0.05 mg/kg, 0.1 mg/kg, 0.25 mg/kg, 0.5 mg/kg, 1 mg/kg, 2.5 mg/kg, 3.5 mg/kg, 5 mg/kg, 6.5 mg/kg, 7.5 mg/kg, 10 mg/kg, 15 mg/kg or 20 mg/kg. In some embodiments, the amount of lasofoxifene or a pharmaceutically acceptable salt thereof (alone or in combination with another agent) includes at least about any of 0.01 mg/kg/day, 0.05 mg/kg/day, 0.1 mg/kg/day, 0.25 mg/kg/day, 0.5 mg/kg/day, 1 mg/kg/day, 2.5 mg/kg/day, 3.5 mg/kg/day, 5 mg/kg/day, 6.5 mg/kg/day, 7.5 mg/kg/day, 10 mg/kg/day, 15 mg/kg/day or 20 mg/kg/day.

In some embodiments, the amount of the other agent (e.g., an EGFR kinase inhibitor or functional equivalent detailed herein or a HER2 inhibitor or functional equivalent detailed herein) includes at least about any of 0.01 mg/kg, 0.05 mg/kg, 0.1 mg/kg, 0.25 mg/kg, 0.5 mg/kg, 1 mg/kg, 2.5 mg/kg, 3.5 mg/kg, 5 mg/kg, 6.5 mg/kg, 7.5 mg/kg, 10 mg/kg, 15 mg/kg or 20 mg/kg. In some embodiments, the amount of lasofoxifene or a pharmaceutically acceptable salt thereof (alone or in combination with another agent) includes at least about any of 0.01 mg/kg/day, 0.05 mg/kg/day, 0.1 mg/kg/day, 0.25 mg/kg/day, 0.5 mg/kg/day, 1 mg/kg/day, 2.5 mg/kg/day, 3.5 mg/kg/day, 5 mg/kg/day, 6.5 mg/kg/day, 7.5 mg/kg/day, 10 mg/kg/day, 15 mg/kg/day or 20 mg/kg/day.

Exemplary dosing frequencies for lasofoxifene or a pharmaceutically acceptable salt thereof (and for the other agent (e.g., an EGFR kinase inhibitor or functional equivalent detailed herein or a HER2 inhibitor or functional equivalent detailed herein)) include, but are not limited to, once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of lasofoxifene or a pharmaceutically acceptable salt thereof (and for the other agent (e.g., an EGFR kinase inhibitor or functional equivalent detailed herein or a HER2 inhibitor or functional equivalent detailed herein)) can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the individual is treated for at least about any of one, two, three, four, five, six, seven, eight, nine, or ten treatment cycles.

The dosing frequency of the other agent can be the same or different from that of lasofoxifene or a pharmaceutically acceptable salt thereof. Exemplary frequencies are provided above.

Lasofoxifene or a pharmaceutically acceptable salt thereof (and the other agent) described herein can be administered to an individual (such as human) via various routes, including, for example, oral, intravenous, intra-arterial, intraperitoneal, intrapulmonary, inhalation, intravesicular, intramuscular, intra-tracheal, subcutaneous, intraocular, intrathecal, transmucosal, and transdermal. In some embodiments, sustained continuous release formulation of the composition may be used.

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit and/or delay the development of the disease.

As will be understood by those of ordinary skill in the art, the appropriate doses of other agents will be approximately those already employed in clinical therapies wherein the other agent are administered alone or in combination with other agents. Variation in dosage will likely occur depending on the condition being treated. As described above, in some embodiments, the other agents may be administered at a reduced level.

Compositions, Kits, and Medicines

The invention also provides compositions (such as pharmaceutical compositions), medicine, kits, and unit dosages useful for methods described herein. Also provided are any use described herein whether in the context of use as a medicament and/or use for manufacture of a medicament.

Provided is a pharmaceutical composition comprising an effective amount of lasofoxifene, or a pharmaceutically acceptable salt thereof, and at least one additional agent selected from the group consisting of tamoxifen or functional equivalent thereof, an EGFR kinase inhibitor (e.g., gefitinib, erlotinib, icotinib, afatinib, neratinib, dacomitinib, osimertinib, rociletinib or olmutinib, or a pharmaceutically acceptable salt thereof) or a functional equivalent thereof, and a HER2 inhibitor (e.g., trastuzumab, pertuzumab, lapatinib, or ado-trastuzumab emtansine (T-DM1), or a pharmaceutically acceptable salt thereof) or a functional equivalent thereof.

In some embodiments, provided is a pharmaceutical composition comprising an effective amount of lasofoxifene, or a pharmaceutically acceptable salt thereof, and at least one additional agent selected from the group consisting of an EGFR kinase inhibitor (e.g., gefitinib, erlotinib, icotinib, afatinib, neratinib, dacomitinib, osimertinib, rociletinib or olmutinib, or a pharmaceutically acceptable salt thereof) or a functional equivalent thereof, and a HER2 inhibitor (e.g., trastuzumab, pertuzumab, lapatinib, or ado-trastuzumab emtansine (T-DM1), or a pharmaceutically acceptable salt thereof) or a functional equivalent thereof.

The composition in some embodiments may be present in a unit dosage form (such as an oral unit dosage form). Suitable unit dosage forms include, but are not limited to, capsules, tablets, pills, caplets, gels, liquids (e.g., suspensions, solutions, emulsions), powders or other particulates, and so forth.

In some embodiments, the dosage of lasofoxifene or a pharmaceutically acceptable salt thereof is about 0.25-50 mg per day.

In another aspect, there are provided kits comprising lasofoxifene or a pharmaceutically acceptable salt thereof and the other agent (e.g., an EGFR kinase inhibitor or functional equivalent detailed herein or a HER2 inhibitor or functional equivalent detailed herein) either in separate containers or in the same container. Kits of the invention include one or more containers comprising lasofoxifene or a pharmaceutically acceptable salt thereof (or unit dosage forms and/or articles of manufacture) and/or at least one other agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kit comprises a) an effective amount lasofoxifene or a pharmaceutically acceptable salt thereof, and b) an effective amount of at least one other agent selected from the group consisting of an EGFR kinase inhibitor (e.g., gefitinib, erlotinib, icotinib, afatinib, neratinib, dacomitinib, osimertinib, rociletinib or olmutinib, or a pharmaceutically acceptable salt thereof) or functional equivalent thereof and a HER2 inhibitor (e.g., trastuzumab, pertuzumab, lapatinib or ado-trastuzumab emtansine (T-DM1), or a pharmaceutically acceptable salt thereof) or functional equivalent thereof. In some embodiments, the kit further comprises instructions for administering lasofoxifene or a pharmaceutically acceptable salt thereof and the other agents simultaneously, sequentially, or concurrently for treatment of cancer (e.g., a ER-α36 positive cancer) (or other uses described herein).

Lasofoxifene or a pharmaceutically acceptable salt thereof and the other agents can be present in separate containers or in a single container. It is understood that the kit may comprise one distinct composition (a single composition comprising lasofoxifene or a pharmaceutically acceptable salt thereof and another agent) or two or more compositions wherein one composition comprises lasofoxifene or a pharmaceutically acceptable salt thereof and one composition comprises another agent.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of lasofoxifene or a pharmaceutically acceptable salt thereof generally include information as to dosage, dosing schedule, and route of administration for the intended treatment. The containers may be unit doses, bulk packages (e.g., multi-dose packages) or sub-unit doses. For example, kits may be provided that contain sufficient dosages of lasofoxifene or a pharmaceutically acceptable salt thereof as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of lasofoxifene or a pharmaceutically acceptable salt thereof and pharmaceutical compositions and instructions for use and packaged in quantities sufficient for storage and use in pharmacies, for example, hospital pharmacies and compounding pharmacies.

In one aspect, the invention provides a kit comprising (i) a composition comprising lasofoxifene or a pharmaceutically acceptable salt thereof; and (ii) an agent for determining presence of an ER-α36 peptide or ER-α36 mRNA. In some embodiments, the kit comprises an agent for determining presence of an ER-α36 peptide, for example, an antibody recognizing the ER-α36 peptide. In some embodiments, the kit comprises an agent for determining presence of an ER-α36 mRNA, for example, an oligonucleotide for quantitative measurement of ER-α36 mRNA.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

Example 1 Chemical Synthesis of Lasofoxifene (5,6,7,8-tetrahydro-6-phenyl-5-[4-[2-(1-pyrrolidinyl) ethoxy]phenyl]-2-naphthalenol)

Lasofoxifene can be prepared as described in PCT/CZ2008/000058, WO2008/145075 A2, incorporated herein by reference, or using steps detailed below.

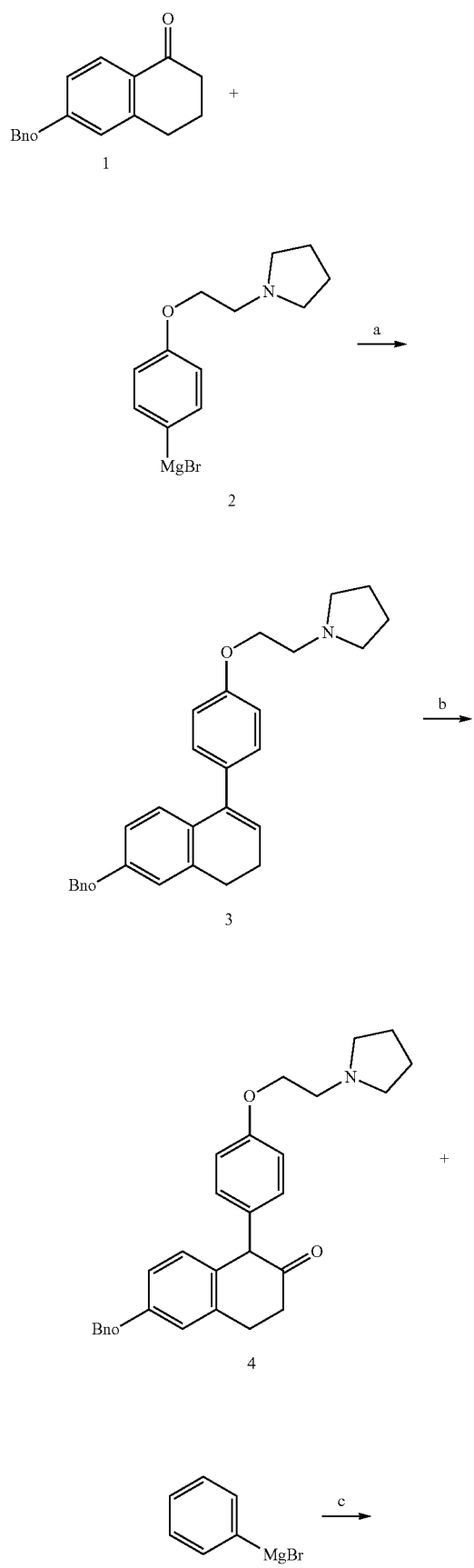

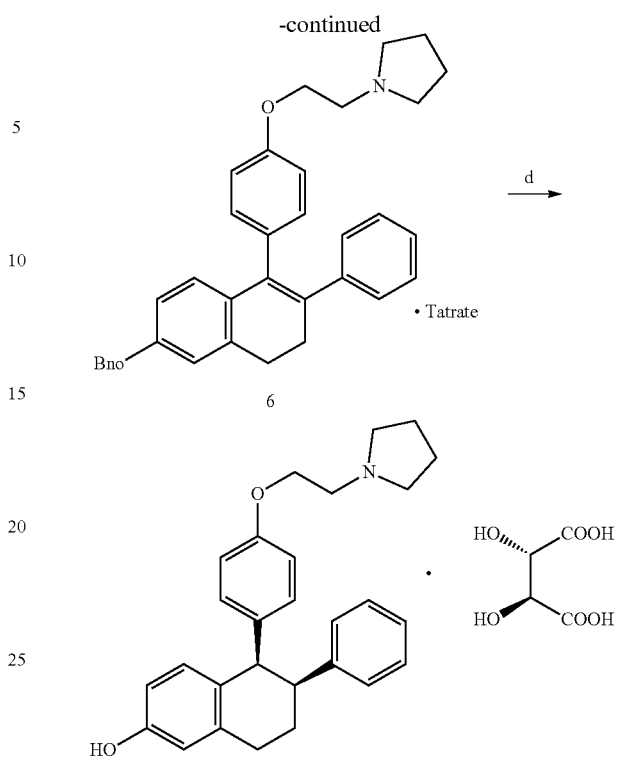

Step a

Preparation of Grignard reagent: magnesium (5.83 g, 240 mmol) and 50 ml of dried THF was added in a 500-mL three-necked flask and stirred overnight under nitrogen atmosphere. A portion of 4-[2-Pyrrolidinoethoxy]phenyl bromide 2 in THF was added dropwise, after the reaction was initiated by heat, the rest of 2 (62.1 g, 230 mmoL) and THF (350 mL) were added slowly between 20 and 30° C. to give the Grignard reagent as a gray solution.

To the refluxing solution of 6-(Benzyloxy)-3,4-dihydro-1(2H)-naphthalenone 1 (34.2 g, 136 mmol) in dried THF (120 mL) was added into the above Grignard reagent within 30 min. The resulting mixture was further refluxed for 30 min, and then cooled down to room temperature and quenched with aqueous saturated $NH_4Cl$ (400 mL). The mixture was extracted with ethyl acetate (160 mL×2), and the combined extracts were washed with water (20 mL×2), dried with anhydrous $Na_2SO_4$, and finally evaporated. The residue was dissolved in 2.0 M aq. HCl, and extracted with isopropyl ether (120 mL×2). The aqueous phase was combined and adjusted to pH 11-12 with 2 M aq. NaOH (21 mL), then extracted with ethyl acetate (160 mL×2). The organic layer was washed with saturated brine (200 mL) and dried over anhydrous $Na_2SO_4$, and evaporated to afford 6-benzyloxy-1-{4-[2-(pyrrolidin-1-yl)ethoxy]phenyl}-3,4-dihydronaphthalene 3 as an oil.

Step b

To the solution of 5 (30.6 g, 72 mmol) in CH2Cl2 (100 ml), a solution of m-CPBA (18.6 g, 108 mmol) in CH2Cl2 (186 ml) was added at 0-5° C. for 1 h and stirred for 1.5 h. The reaction was quenched with aqueous solution of Na2SO3 (5.12 g, 40.6 mmol), and basified by 2 M aq. NaOH (21 mL) to pH 10-11. The two layers were separated and the organic layer was washed with saturated brine (50 mL×2), dried over anhydrous Na2SO4 (12.1 g), and evaporated to give 6-benzyloxy-1-[4-(2-(pyrrolidin-1-yl)ethoxy)phenyl]-3,4-dihydronaphthalen-2(1H)-one 4 (29.0 g, 90.0%).

Step c

To a suspension of cerium chloride (12.3 g, 33.0 mmol) in THF (80 mL) was added a solution of compound 4 (12.8 g, 30.1 mmol) in THF (45 mL) at 0° C. under nitrogen atmosphere. The resulting mixture was stirred for 1.5 h at that temperature, and further cooled down to −10 to −5° C. A solution of phenyl magnesium bromide in dried THF was added. [The Grignard reagent was freshly prepared from bromobenzene (5.21 g, 33.2 mmol) and magnesium turnings (0.820 g, 33.7 mmol) in THF (40 mL)], The mixture was further stirred for 2 h and quenched with aqueous aq. NH4Cl (80 mL). Cerium chloride was separated by filtration and the filtrate was extracted with CH2Cl2 (120 mL×2), and the combined organic layers were washed with saturated brine. The extract was evaporated to leave a yellowish oil, which was treated with D-Tatrate in MeOH to yield 6-benzyloxy-2-phenyl-1-{4-[2-(pyrrolin-1-yl)ethoxy)]phenyl}-3,4-dihydronaphthalene tatrate 6 as a solid.

Step d

An autoclave was charged with 6 (1.5 g), 5% Pd/C (0.32 g) in the mixture of EtOH and MeOH. The vessel was sealed and then the mixture was stirred for 10 h at 50° C. under hydrogen atmosphere (10 atm pressure). After completion of the reaction, the reaction mixture was cooled to room temperature and filtered through a celite and washed with methanol (20 mL). The filtrate was concentrated under reduced pressure to provide the desired product 1-{2-[4-(6-benzyloxy-2-phenyl-1,2,3,4-tetrahydro-naphthalen-1-yl)-phenoxy]ethyl}pyrrolidine. Yield: 0.736 g (85%). The crude product was recrystallized in ethanol to get the desired product (Lasofoxifene).

Step e

Purified lasofoxifene (2 g) from step d was dissolved in 20 mL of 95% ethanol, and mixed together with 0.78 g D-tartaric acid, which is dissolved in 7.8 mL of 95% ethanol. The mixed solution was carefully heated to slight reflux for 5 minutes, and then cooled to room temperature. About 1.4 g precipitation of lasofoxifene D-tartrate salt was obtained (Yield 50%).

Lasofoxifene D-tartrate was dissolved in DMSO-$d_6$ (50 mg/mL) for NMR analysis. $^1$H NMR (600 MHz, DMSO-$d_6$) δ 1.71-1.85 (m, 5H), 2.08 (s, 1H), 2.90-2.99 (m, 6H), 3.17 (br, 2H), 3.295 (m, 1H), 4.02-4.06 (m, 4H), 4.17 (d, J=3.6 Hz, 1H), 4.43 (br, 2H), 6.6 (m, 5H), 6.81 (d, J=6.4 Hz, 2H), 7.11 (s, 1H), 7.13 (s, 2H). $^{13}$C NMR (150 MHz, DMSO-$d_6$) δ 174.26, 155.74, 155.36, 144.12, 137.08, 135.37, 131.09, 130.97, 130.04, 127.83, 127.61, 125.87, 114.35, 113.58, 112.91, 71.90, 64.07, 53.59, 53.100, 49.40, 44.41, 29.244, 22.56, 22.41.

Step f

A suspension of 20 mg of lasofoxifene D-tartrate salt in 5 mL of 95% aqueous ethanol was heated at 60° C. in a single-necked flask until the mixture turned clear. The solution was carefully filtered at 60° C. The filtrate was placed in dark for two days. The fine crystals formed were collected for X-ray analysis.

Example 2 General Materials and Methods for Biological Experiments

ER-α66, ER-β and GPER1 antibodies were purchased from cell signal transduction (CST) and santa cluz. Fetal bovin serum (FBS), medium and L-glutamine, anti-fungi and antibiotics were purchased from life science. Tamoxifen (MPG USP GRADE) were offered by Okahata (Shanghai) Trading Co., Ltd. All compounds were purchased from Sigma or Aladdin. Mice food was made by Trophic Animal Feed High-tech Co., Ltd, Nantong, China. Nude mice were purchased from BK animal Inc.

Preparation of ER-α36 Antibody and Plasmid

The last 27 amino acid of ER-α36 was synthesized and cross-linked with BSA by GL Biochem Inc. (China). Anti-rabbit serum was prepared by Abgent (China). The construction of pEGFP-GPER1 plasmid was described previously.

Cell Culture, Extraction of Cellular Lysate and Western Blotting Assay

HEK-293, MCF-7, MDA-MB-231, HBE, H1299 and H460 cells were grown following ATCC protocol. The expression level of estrogen-bound receptors was measured using western blotting. Briefly, 80-90% confluence cells were harvested and lysed in RIPA buffer or 1×PBS containing 1% triton-x-100 and protease inhibitor cocktail. Total protein concentration was measured using Bio-rad protein staining dye. Western blotting was performed following standard protocol using nitrocellulose membrane (Millipore) and Bio-rad semi-dry transfer system. The equal amount of total protein from cell lysate was loaded to SDS-PAGE for western blotting. The expression level of ER-α36 and 66, ER-β and GPER1 was measured using antibody.

Measurement of the Cytosolic $Ca^{2+}$ Concentrations

The assays were performed as following. Briefly, cells were grown on a glass-bottomed perfusion chamber mounted on the stage of an inverted confocal microscope (Andor), and then incubated with 2 μM Fura-red AM (Molecular Probes, Eugene, Oreg., USA) for 60 min at 37° C. in normal culture media. Cells were then perfused continuously with Hanks' balanced salt solution (Sigma) containing 1.8 mM $CaCl_2$ and 0.8 mM $MgCl_2$, pH 7.4. The fluorescence density was recorded when data revealed that the $Ca^{2+}$ concentration had changed. Cells were perfused with complete culture media without phenol red, and Fura-red was excited at 572 nm. The fluorescence emitted at 657 nm was then collected and recorded using a CCD-based imaging system running software (Andor).

Measurements of Drug Activity to Inhibit Cell Division

Cells were inoculated into 24 well plates with culture medium and treated using the designated concentration of drugs. Cell number was counted using a cell counter (Count Star). The cell bio-behaviors including total cell number and movement were measured using a real-time cell monitoring system. Briefly, the image was captured at 5 min intervals for 66 h. Cell morphological parameters and the movement of each individual cell was calculated following manufacture's instruction.

Inducing Tamoxifen-Resistance MCF-7 Cells

MCF-7 cells were grown in EMEM medium containing 10% FBS, antibiotics and 0.1 μM tamoxifen for three months. And then increase tamoxifen concentration to 0.5 μM for another three months, Finally, MCF-7 cells were grown in EMEM medium containing 10% FBS, antibiotics and 1 μM tamoxifen for four months. Tamoxifen-resistance MCF-7 cells were tested by counting cell proliferation rate when cells were grown in high concentration tamoxifen.

Generation of Xenograft Tumors in Nude Mice and Drug Inhibition Assay

H460 cells were grown in RPMI-1640 medium containing 10% FBS. When cells are 70-80% confluent and ready for experiments, replace medium with fresh medium for 3 hours. Remove medium and wash cells with medium without FBS for three times. Cells were then trypsinized and suspended in medium, equal volume of cells and support gel was mixed up to 200 μl for each injection. Cells were injected subcutaneously (s.c.) into 4-6 week old nude mice. 1.0~2.0×10$^6$ H460 cells were administrated into each nude mouse. When the tumors have reached an average volume of ~50-60 mm$^3$, drugs were intragastrically administrated daily. Tumor size were calculated by the formula: volume= (width)$^2$×length/2.

Animals

Nude mice were purchased from the Shanghai B K Animal Model Inc. Ltd., China. The animal experimental protocol was approved by Animal Ethics Committee of the Shanghai Institute of Planned Parenthood Research (SIPPR Regulation$^\#$2015-13), in accordance with the 588$^{th}$ regulation of animal experiments issued by Chinese Government in 2011. All animal experiments were performed under audit of the SIPPR Animal Ethics Committee.

Statistical Analysis

In tables and figures, the results were presented as mean±SD. Asterisks indicate a statistically significant difference calculated using student's t-test, two-tailed from at least three repeats or N≥6.

Figure 2:
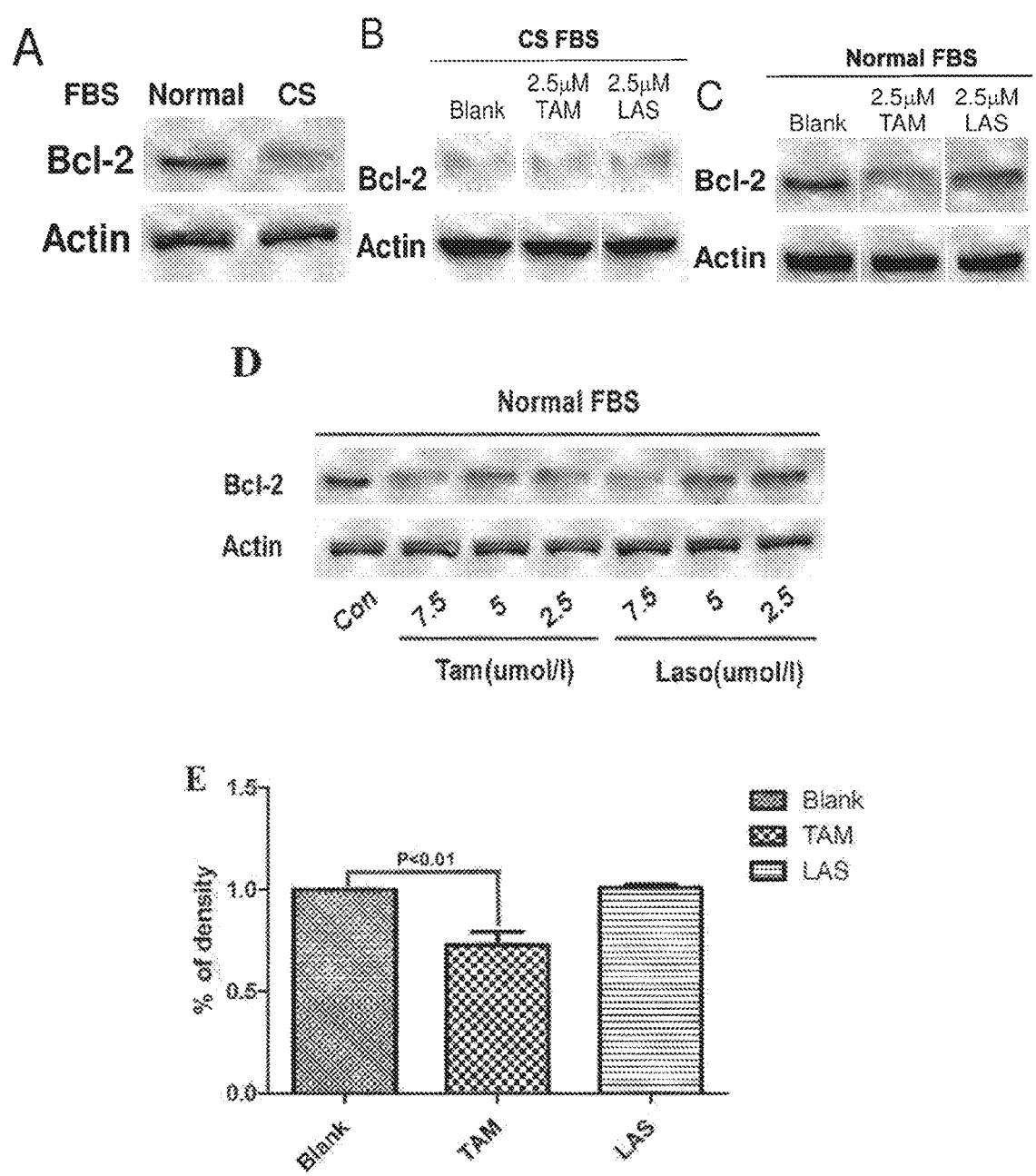
FIG. 2: Inhibition of Bcl-2 expression in MCF-7 cells by lasofoxifene in comparison with tamoxifen. A: MCF-7 cells were cultured in either EMEM medium containing 10% FBS (Normal) or 5% charcoal striped FBS (CS) for 72 hours. Western blotting assay were performed to analyze Bcl-2 expression (CS: charcoal striped). B: MCF-7 cells were cultured in EMEM medium containing insulin and 5% charcoal striped FBS for 72 hours and then treated by lasofoxifene and tamoxifen for 48 hours. Western blotting assay were performed to analyze Bcl-2 expression. C. MCF-7 were cultured in EMEM medium containing insulin and 10% FBS for 72 hours and then treated by lasofoxifene and tamoxifen for 48 hours. Western blotting assay were performed to analyze Bcl-2 expression. D. Lasofoxifene-inhibited Bcl-2 expression in a dosage dependent manner (same conditions as in part C). E. Statistical analysis of three repeats of part C. N=3×3.

Example 3 Lasofoxifene Inhibited Estrogen Classic Nuclear Pathway Weakly Compared with Tamoxifen Estrogen and ER complex binds to estrogen response element (ERE) in chromosome to regulate RNA transcription. Bcl-2 is a key member of anti-apoptosis family proteins. Its overexpression has been linked to many kinds of cancers in human being. The Bcl-2 promoter contains an ERE sequence, and Bcl-2 mRNA expression in MCF-7 cells has been found to be positively regulated by E2 and inhibited by tamoxifen (Gennari L. Drugs Today (Barc). 2006 June; 42(6):355-67.) Lasofoxifene selectively binds to both estrogen receptor subtypes (ER-α or ER-β) with at least 10-fold higher affinity than those reported for raloxifene and tamoxifen (Gennari L. Drugs Today (Barc). 2006 June; 42(6):355-67). We first assessed whether lasofoxifene inhibited Bcl-2 expression at higher efficiency compared to tamoxifen. MCF-7 cells were grown in DMEM medium containing insulin and 10% FBS or 5% charcoal striped FBS for 72 h. Cells were then treated by lasofoxifene and tamoxifen for 48 h. We confirmed previous study that the expression of Bcl-2 protein was enhanced by culture medium containing estrogen compared with that containing charcoal-stripped (CS) FBS (FIGS. 2A and B, Blank). Surprisingly, lasofoxifene showed weaker activity to inhibit Bcl-2 expression compared with tamoxifen (FIG. 2C, 2.5 μM TAM: 2.5 μM LAS). Importantly, neither tamoxifen nor lasofoxifene affected Bcl-2 expression compared with vesicle (Blank) in cells cultured in medium without estrogen (Charcoal stripped (CS) FBS in phenol red (PR)-free EMEM medium; FIG. 2B CS FBS panel). These results indicated that lasofoxifene blocked the estrogen classic nuclear pathway weakly compared with tamoxifen; and that lasofoxifene may inhibit MCF-7 cell proliferation via different estrogen-modulated pathway.

Example 4 Lasofoxifene Inhibited the Proliferation of MCF-7 Cells More Sensitively Compared with Tamoxifen when it Positively Expressed ER-α36

Figure 3:
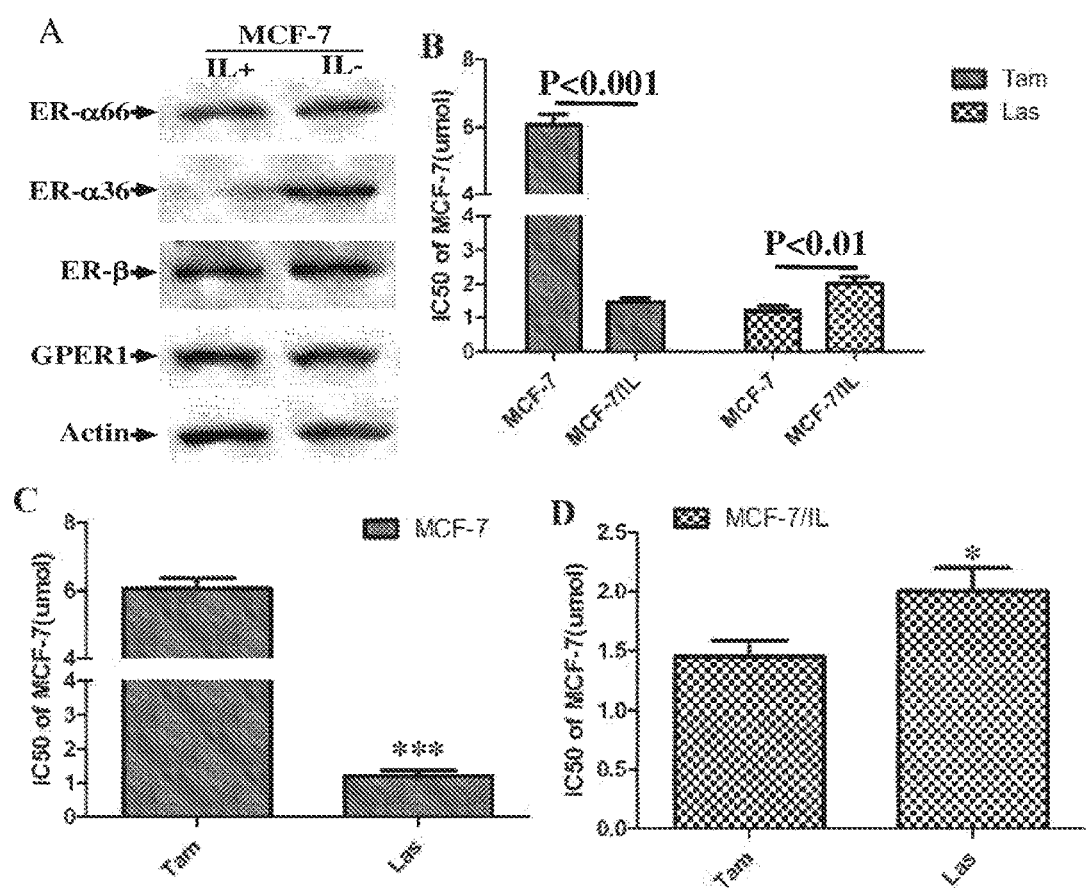
FIG. 3: Inhibition of proliferation of ER-α36 positive MCF-7 cancer cells by lasofoxifene in comparison with tamoxifen. A. MCF-7 cells were grown in insulin-free (IL-) medium for three months. Expression of ER-α66, ER-α36, ER-β and GPER were tested using Western blot. B. MCF-7 cells, after cultured in either medium with insulin or without insulin, were treated with tamoxifen or lasofoxifene. Graph shows IC$_{50}$ (μM) of MCF-7 cells treated by either drug under both conditions. C. It compares IC$_{50}$ (μM) of MCF-7 cells responding to tamoxifen or lasofoxifene at the condition of pre-cultured in medium without insulin. *** indicates $P<0.001$. D. Graph compares IC$_{50}$ (μM) of MCF-7 cells responding to tamoxifen or lasofoxifene at the condition of pre-cultured in medium with insulin. * indicates $P<0.05$.

The transcription variant of ER-α36 lacks the AF-1 and AF2 domains. It contains a partial ligand binding domain and a palmitoylation motif (445-453), and possesses a unique C-terminal 27 amino acid sequence in place of the typical 140 amino acids (456-595) of full-length ER-α. It was found located at plasma membrane and cytosol (Boonyaratanakornkit, V. Steroids. 2011 August; 76(9):877-84). Since ER-α36 is restricted to modulating MIES and was found to be uniquely expressed in tamoxifen-resisted cancer cells, such as MDA-MB-231, ER-α36 is thought to be responsible for the tamoxifen-resistance (Kang L, et al. Mol Endocrinol. 2010 April; 24(4):709-21; Rao J, et al. J Steroid Biochem Mol Biol. 2011 November; 127 (3-5):231-7.) Moreover, insulin (IL) binds to insulin receptor (IR), stimulating the phosphorylation of insulin receptor substrate (IRS). Phosphorylated IRS interacts with dimer estrogen-ER complexes, which can then translocate into the nucleus and bond with ERE sequence to regulate RNA transcription through the estrogen classical nuclear pathway. The proliferation of MCF-7 cells is modulated by IL, and the sensitivity of these cells to tamoxifen is increased after the temporary removal of IL from culture medium (Butler W B et al. Cancer Res. 1981 January; 41(1):82-8) or when IRS expression was transiently knocked down using IRS-specific siRNA (Cesarone G, et al. J Cell Biochem. 2006 May 15; 98(2):440-50.) Taken together, it indicates that insulin may regulate tamoxifen sensitivity in MCF-7 cells. We grew MCF-7 cells in insulin-free medium for 3 months and we found that the transcription variant of ER-α36 was up-regulated in insulin-free medium. In contrast, the expression levels of other estrogen receptors were not affected (FIG. 3A). MCF-7 cells grown in medium with or without IL showed distinct patterns responding to the treatment of lasofoxifene or tamoxifen shown by the IC$_{50}$ (μM) of MCF-7 cells. (FIGS. 3B-D) Lasofoxifene more effectively inhibited divisions of MCF-7 cell which positively expressed ER-α36 (FIG. 3B, right). On the other hand, Tamoxifen exerted the opposite effect (FIG. 3B, left). When MCF-7 cells positively expressed ER-α36 (MCF-7), lasofoxifene more effectively inhibited ER-α36+MCF-7 cell division compared with tamoxifen. (FIG. 3C) On the other hand, when MCF-7 cells did not express ER-α36 (MCF-7/IL), lasofoxifene exhibited less activity to inhibit MCF-7 cell division compared with tamoxifen, indicating that overexpressed ER-α36 variant may result in acquired or de novo tamoxifen-resistance.

MCF-7 cells were grown in insulin-free medium for 3 months. The expression level of estrogen-bound receptors was measured using western blotting. Briefly, 80-90% confluence cells were harvested and lysed in RIPA buffer or 1×PBS containing 1% triton-x-100 and protease inhibitor cocktail. Total protein concentration was measured using Bio-rad protein staining dye. Western blotting was performed following standard protocol using nitrocellulose membrane (Millipore) and Bio-rad semi-dry transfer system. The equal amount of total protein from cell lysate was loaded to SDS-PAGE for western blotting. The expression level of ER-α36, ER-α66, ER-β and GPER1 was measured using antibodies purchased from Cell Signal Transduction (CST) and Santa Cruz.

Figure 4:
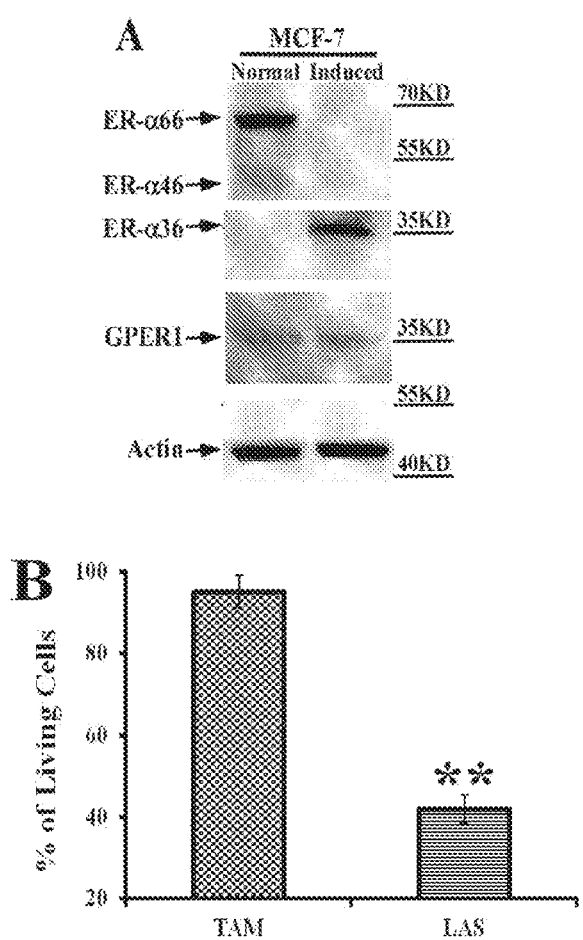
FIG. 4: Inhibition of proliferation of acquired tamoxifen-resistance MCF-7 cells by lasofoxifene. A. MCF-7 cells were treated with tamoxifen for ten months. Expression of ER-α66, ER-α46, ER-α36, GPER-1 were tested using Western blot. B. After MCF-7 cells were treated with tamoxifen for ten months, cells were treated with either 2 μM tamoxifen or 2 μM lasofoxifene. Proliferation of MCF-7 were shown under each treatment. ** indicates $P<0.01$.
Figure 6:
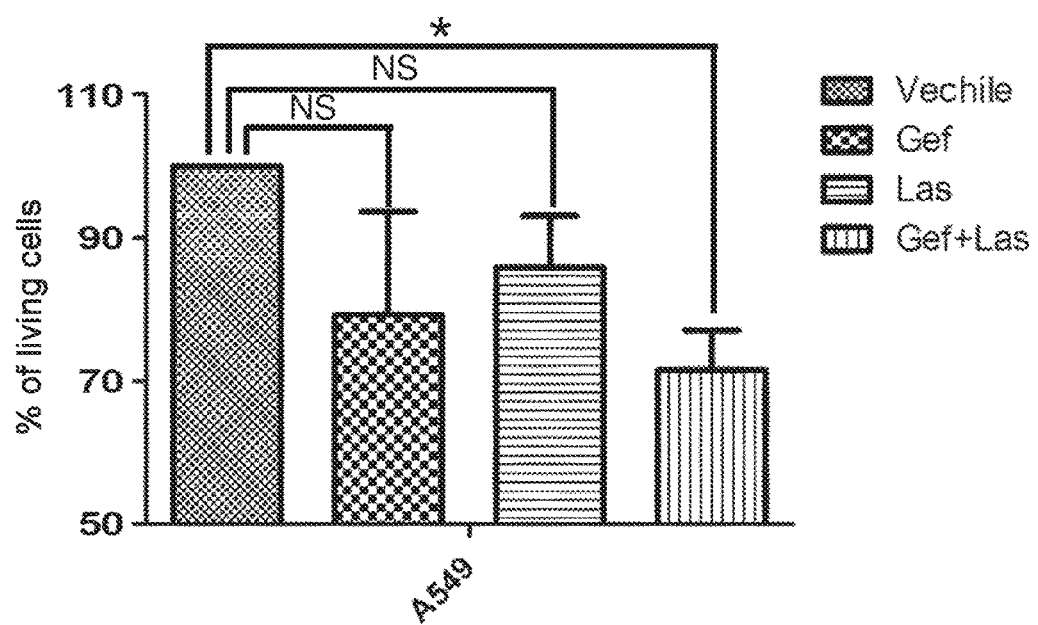
FIG. 6: Inhibition of proliferation of Ras mutation in A549 lung cancer cells by a combination of lasofoxifene and gefitinib. N=3×3; * means $P<0.05$; NS: non-significantly different.

Example 5 Inhibition of Proliferation of Acquired Tamoxifen-Resistance MCF-7 Cells by Lasofoxifene To verify our hypothesis that overexpressed ER-α36 variant may result in acquired de novo tamoxifen-resistance, we induced MCF-7 cells using tamoxifen for ten months. We found the expression of ER-α66 was decreased (FIG. 3A, top panel). In contrast, the expression level of ER-α36 was enhanced (FIG. 4A, middle panel). The expression level of GPER1 was not affected (FIG. 4A bottom panel). 2 μM tamoxifen did not inhibit MCF-7 cell proliferation induced by tamoxifen for over 10 months. In contrast, 2 µM lasofoxifene showed over 50% inhibiting activity under the same testing condition (FIG. 4B). It indicated that lasofoxifene is ER-α36 antagonist to inhibit the proliferation of tamoxifen-resistant and ER-α36+ breast cancer.

Example 6 Lasofoxifene Inhibited Proliferation of Tumor Cells Expressing ER-α36 (De Novo or Acquired)

Figure 8:
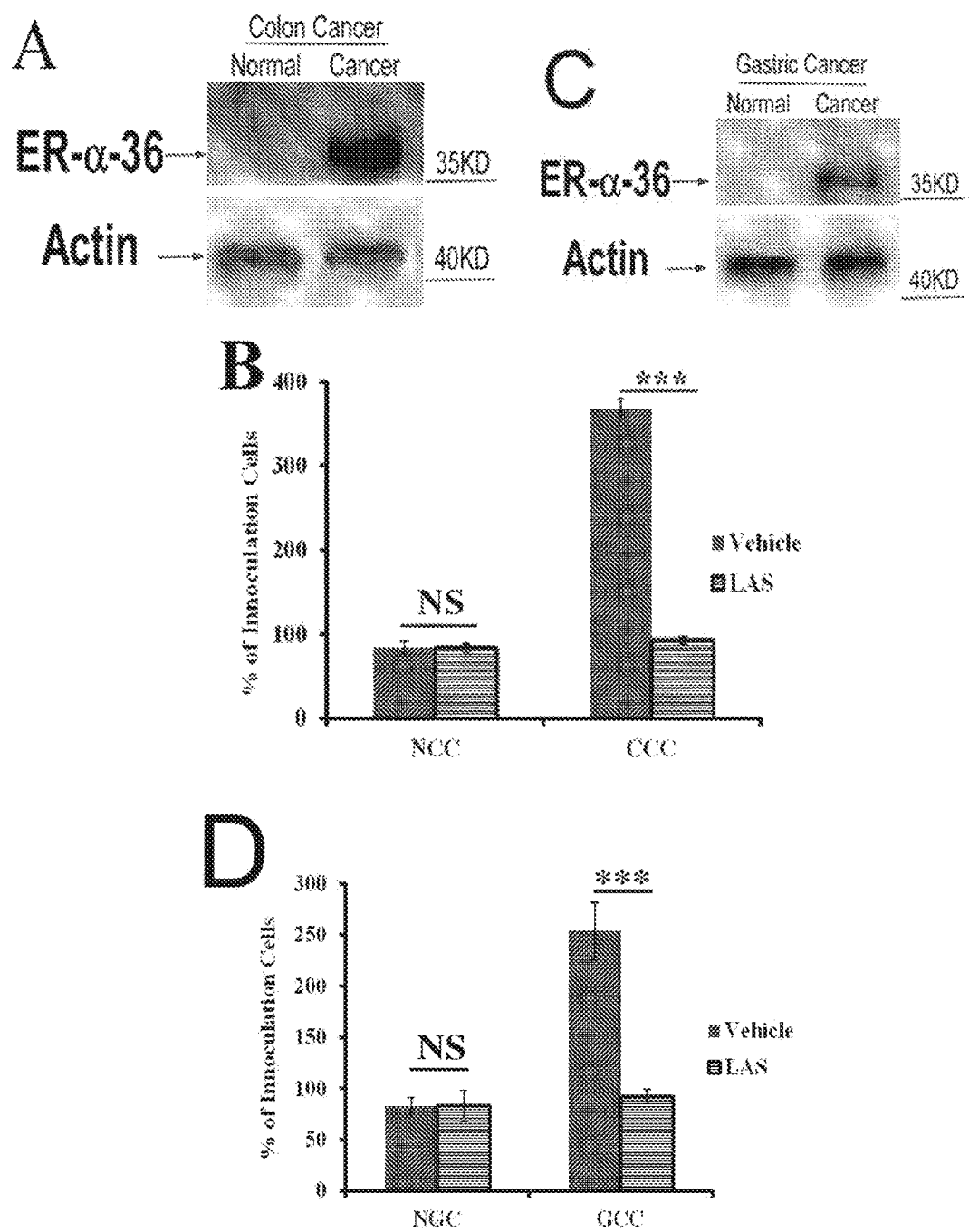
FIG. 8: Inhibition of proliferation of ER-α36 positive colon and gastric cancer cells. A: ER-α36 was positively expressed in colon cancer cells. B: Lasofoxifene inhibited colon cancer cell division. NCC: normal colon cells. CCC: colon cancer cells. C: ER-α36 was positively expressed in gastric cancer cells. D: Lasofoxifene inhibited gastric cancer cell division. NGC: normal gastric cells. GCC: gastric cancer cells. N=3×3; *** means $P<0.001$.
Figure 9:
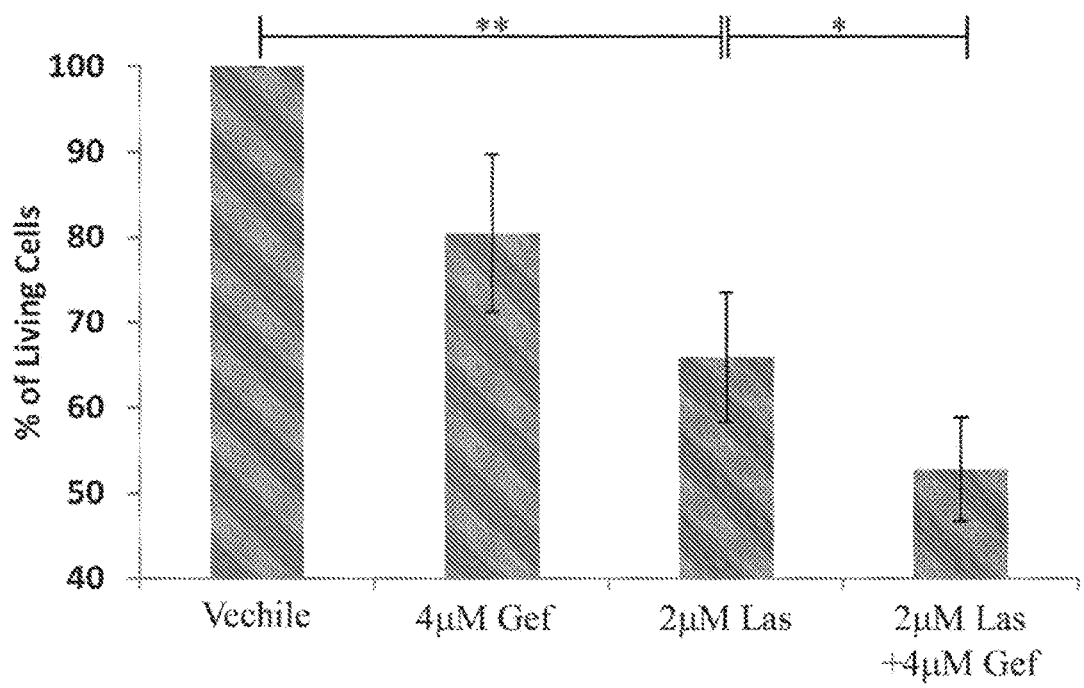
FIG. 9: Inhibition of proliferation of ER-α36 positive/triple negative MDA-MB231 breast cancer cells. MDA-MB231 cells treated with lasofoxifene in DMEM medium containing 10% FBS. N=3×3; * and ** mean $P<0.05$ and $P<0.01$, respectively.
Figure 10:
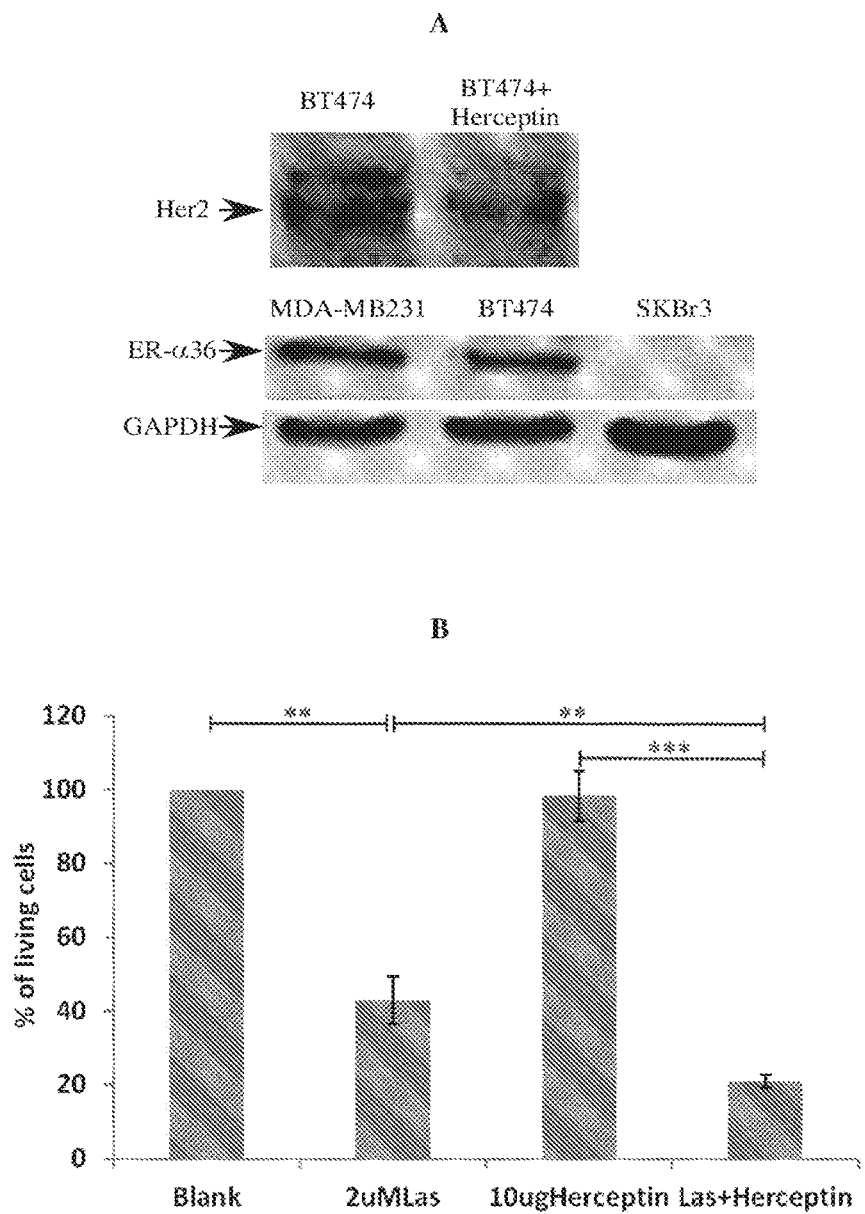
FIG. 10: Inhibition of proliferation of Heceptin-resistance BT474 breast cancer cells. BT474 breast cancer cells were treated with 10 μg/ml Herceptin® in medium for 3 months. A. Cells positively expressed of ER-α36, and decreased the expression level of HER2. B. Sensitive response to 2 μM lasofoxifene. Combine administration of lasofoxifene and Herceptin® inhibited BT474 cell proliferation more efficiency as compared with single using either lasofoxifene and Herceptin. * and ** mean $P<0.01$ and $P<0.001$, respectively.

The epidemiologic data demonstrates that women have a higher risk of non-small cell lung cancer (NSCLC) and a lower risk of lung cancer mortality compared with women with breast cancer treated by anti-estrogenic therapy and men after excluding smoking effect (Ramchandran K et al. Semin Oncol 2009, 36:516-523; Kiyohara C et al. Gender Medicine 2010, 7:381-401; Bouchardy C et al. Cancer 2011, 117:1288-1295.) It indicates that ER-α36 may be overexpressed in some lung cancer cells. We thus tested the expression of ER-α36 from lung cancer cells. After screening the expression of ER-α66, ER-α36, GPER1 and EGFR, we found that HBE cells did not expression ER-α36. H1299 cells expressed high level of ER-α36, but not EGFR. H460 cells expressed high level of both ER-α36 and EGFR (FIG. 5-A). The proliferation of H460 and H1299 cells were inhibited under the treatment of 2 µM lasofoxifene (FIGS. 5-B and D). In contrast, tamoxifen exhibited opposite effect (FIG. 5-B). Neither tamoxifen nor lasofoxifene affected the proliferation of HBE cells (FIG. 5-B). The H1299 cells weakly express EGFR compared with that in the H460 cells (FIG. 5A), and the inhibitor of EGFR kinase, gefitinib, did not inhibit H1299 cell proliferation (FIG. 5D). In contrast, it inhibited the proliferation of H460, which positively expressed EGFR (FIG. 5C). In addition, the H460 cells were more sensitive to the combined treatment of lasofoxifene and gefitinib (FIG. 4C). Combined treatment with lasofoxifene and gefitinib in the H1299 cells showed similar effect compared to treatment by lasofoxifene alone (FIG. 4D). In addition, the same lasofoxifene activity was also found when it was used to treat ER-α36+ cancers including colon cancer (FIG. 8-B), gastric cancer (FIG. 8-D), and triple negative breast cancer (FIG. 9). It indicated that lasofoxifene can inhibit the growth of acquired and de novo tamoxifen-resistance or ER-α36+ cancers.

Figure 7:
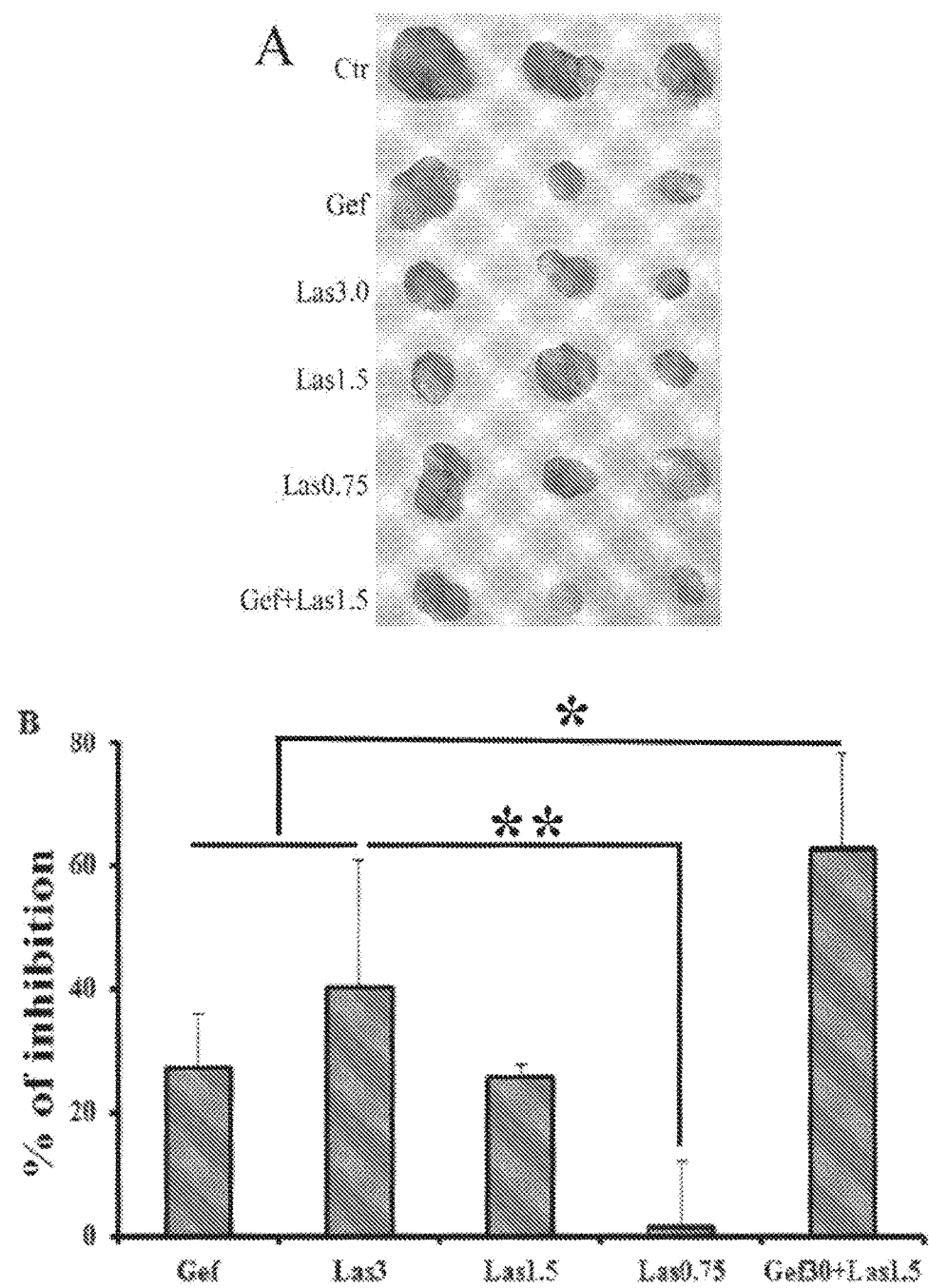
FIG. 7: Activity to Inhibition of growth of xenograft-ER-α36+/EGFR+ lung tumor (H460) in nude mice by lasofoxifene (LAS) and/or gefitinib. A. Nude mice were grafted with H460 cells. Tumor size were shown after treatment with gefitinib, 3 mg lasofoxifene per kilogram of mouse body mass (3 mg/kg, Las3.0), 1.5 mg lasofoxifene per kilogram of mouse body mass (1.5 mg/kg, Las1.5), 0.75 mg lasofoxifene per kilogram of mouse body mass (0.75 mg/kg, Las0.75), or a combination of gefitinib and 1.5 mg lasofoxifene per kilogram of mouse body mass (Gef+Las1.5). B. Statistical result of tumor mass from two repeat experiments (n≥6).* and ** mean $P<0.05$ and $P<0.01$, respectively.

Example 7 Lasofoxifene Inhibited ER-α36 Positive Cancer Growth in Xenograft Nude Mice To verify in vitro results, we constructed xenograft H460 tumors in nude mice. The tumor size was measured using digital vernier caliper. When tumors grew to 60-70 mm$^3$, gefitinib, or lasofoxifene, or a combination of gefitinib and lasofoxifene were administrated to mice daily for 2-3 weeks. We found that lasofoxifene inhibited the growth of xenograft H460 tumors (FIG. 7). In addition, both E2 and EGFR activate ERK/MAPK and AKT/PI3K signal transduction pathways. When mice were administrated with a combination of lasofoxifene and gefitinib, the inhibition effect was even more striking than the administration by lasofoxifene or gefitinib alone (FIG. 7-A, B). Therefore, lasofoxifene inhibits the growth of ER-α36+ cancer. A combined administration of lasofoxifene and gefitinib enhanced the inhibition effect to the growth of ER-α36+ cancer.

Example 8 Lasofoxifene Prevents Osteoporosis Via GPER1 Agonist

Figure 11:
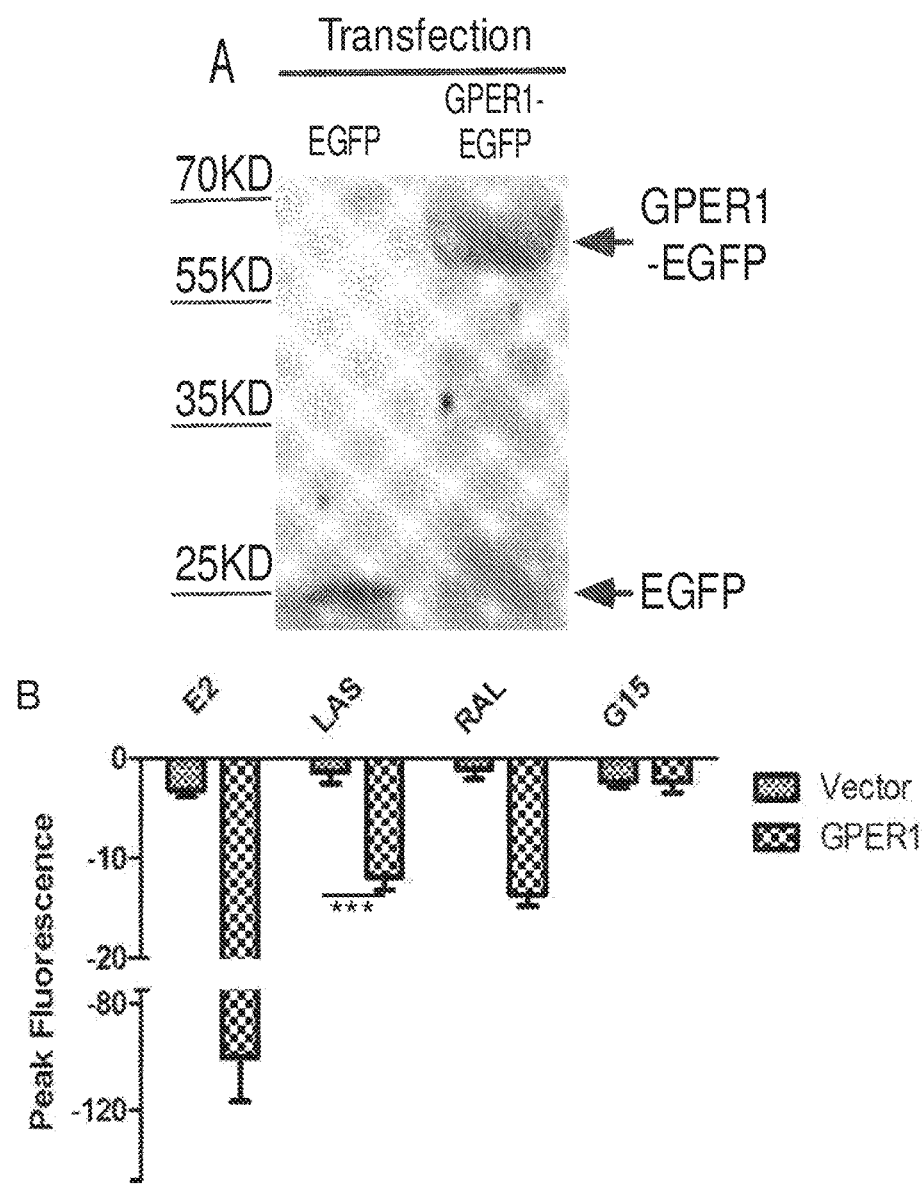
FIG. 11: Prevention of osteoporosis by lasofoxifene as GPER1 agonist. A. HEK293 cells were transfected with either GPER1-EGFP or EGFP alone. Expression of GPER-1EGFP and EGFP were shown using western blot. B. HEK293 cells transfected with GPER1-EGFP or EGFP alone were treated with E2, lasofoxifene (LAS), raloxifene (RAL), or G15 (GPER1 antagonist). Cytosolic [$Ca^{2+}$], were tested using Fura-red as indicator. *** means $P<0.001$.

Both lasofoxifene and raloxifene were marketed as estrogenic agents to prevent osteoporosis in postmenopausal women. Because we already demonstrated that lasofoxifene was an inhibitor of ER-α36 and classic estrogen nuclear pathway; and that E2 binds to GPER1 and regulates Gas signal resulting in enhancing cytosol [Ca$^{2+}$] elevation through InsP$_3$R; we hypothesize that lasofoxifene is GPER1 agonist. GPER1-EGFP was overexpressed in HEK293 cells transiently transfected with GPER1-EGFP plasmid (FIG. 11A). Our results showed that G15, GPER1 antagonist, did not significantly changed cytosolic [Ca$^{2+}$]$_i$ in HEK293 cells overexpressing GPER1-EGFP compared with those cells transfected with the EGFP vector (FIG. 7B). Lasofoxifene and raloxifene significantly enhanced cytosolic [Ca$^{2+}$]$_i$ in HEK293 cells overexpressing GPER1-EGFP (FIG. 11B). Because cytosolic [Ca$^{2+}$]$_i$ signal was considered as the agonist of MIES, and because lasofoxifene and raloxifene elevated cyto-Ca$^{2+}$ signal, lasofoxifene and raloxifene were considered as agonists of GPER1. Therefore, lasofoxifene and raloxifene prevented osteoporosis via activation of GPER1 signal transduction pathway in bone.

Discussion

Lasofoxifene was developed and marketed as a selective estrogen receptor modulator to prevent osteoporosis. It was also reported to prevent breast cancer. However, the mechanism was never reported. The current study indicated that lasofoxifene was a weaker inhibitor to block Bcl-2 expression via estrogen classic nuclear pathway compared with tamoxifen. Interestingly, lasofoxifene was reported to have a 1.5 nM binding affinity to ER-αLBD, suggesting that lasofoxifene may inhibit the biological function of membrane-bound ER at higher efficiency compared with tamoxifen. The current study indicated that lasofoxifene is an ER-α36 antagonist to block the proliferation of ER-α36 positive cancer cells.

Tamoxifen was marketed as an antagonist of estrogen receptor to treat breast cancer patients highly expressing ER. It also induces drug resistance and uterine endometria cancer resulting in the discovery of membrane-bound estrogen receptors, ER-α36 and GPER1. Moreover, MIES was reported to active ERK/MAPK and AKT/PI3K signal transduction pathways, indicating that MIES-induced cancer should be considerate. However, the lack of a full understanding of the molecular mechanisms involved and interfering cross-talk between selective modulators with different membrane-bound estrogen receptors and their signal transduction pathways have made it difficult to clear the physiological function between ER-α36 and GPER1, and design a compound to treat MIES-induced cancers. Current study indicated that lasofoxifene inhibited ER-α36 positive cancer growth, indicating that it is ER-α36 rather GPER1 to induce MIES-induced cancer and acquired or de novo tamoxifen-resistance.

Lasofoxifene was developed as a SERM to prevent osteoporosis in postmenopausal women. The current study indicated that lasofoxifene is GPER1 agonist to enhance Ca$^{2+}$ channel gating of inositol triphosphate receptor (InsP$_3$R) via activation of E2-GPER1 pathway. GPER1 has been found predominately to localize endoplasmic reticular. A previous report was made on cross-talk between GPER1 and IL-IR complex. And enhanced activity of InsP$_3$R was reported to improve glucose uptake. Estrogen was reported to bind to GPER1 and active Gas resulting in enhanced activity of InsP$_3$R Ca$^{2+}$ channel. Mitochondria-associated endoplasmic reticular membrane (MAM) is a major machine of cell metabolite. Therefore, E2 binds to GPER1 could modulate cell metabolic signals. In addition, GPER1 knockout mice demonstrated that GPER1 was required for normal bone growth, glucose homeostasis, and blood pressure in female mice. Thus, GPER1 is an interesting therapeutic target to exploit for the novel treatments of some estrogen-related metabolic diseases in postmenopausal females. Taken together, lasofoxifene prevents osteoporosis in postmenopausal women because it is GPER1 agonist.

In summary, estrogen is a key hormone to regulate normal mammalian physiology, aging and many disease states. Although it is reviewed that estrogen nuclear receptors are described as ligand-activated transcription factors mediating genomic effects in hormonally regulated tissues and diseases, estrogens also mediate rapid signaling events traditionally associated with membrane-bound estrogen receptors (ER-α36) and GPER1 (G protein-coupled estrogen receptor, formerly GPR30). In many instances, the protective or beneficial effects of estrogen are mimicked by SERM to treat estrogen-mediated diseases. We are developing the novel opportunities clinically towards ER-α36- or GPER1-targeted therapeutics. Our data indicate that lasofoxifene is an ER-α36 antagonist of MIES-induced cancer, but weaker antagonist of estrogen classic nuclear pathway compare with tamoxifen. Moreover, it is also a GPER1 agonist to prevent osteoporosis in postmenopausal women.

REFERENCES

1) Revankar C M, Cimino D F, Sklar L A, Arterburn J B, Prossnitz E R. A transmembrane intracellular estrogen receptor mediates rapid cell signaling. Science. 2005 Mar. 11; 307(5715): 1625-30.
2) Wang Z, Zhang X, Shen P, Loggie B W, Chang Y, Deuel T F. Identification, cloning, and expression of human estrogen receptor-α 36, a novel variant of human estrogen receptor-α 66. Biochem Biophys Res Commun 2005, 336:1023-1027.
3) Boonyaratanakornkit, V. Scaffolding proteins mediating membrane-initiated extra-nuclear actions of estrogen receptor. Steroids. 2011 August; 76(9):877-84.
4) Ramchandran K, Patel J D: Sex Differences in Susceptibility to Carcinogens. Semin Oncol 2009, 36:516-523.
5) Kiyohara C, Ohno Y: Sex differences in lung cancer susceptibility: a review. Gender Medicine 2010, 7:381-401.
6) Bouchardy C, Benhamou S, Schaffar R, Verkooijen H M, Fioretta G, Schubert H, Vinh-Hung V, Soria J-C, Vlastos G, Rapiti E: Lung cancer mortality risk among breast cancer patients treated with anti-estrogens. Cancer 2011, 117:1288-1295.
7) Sipponen P and Correa P: Delayed rise in incidence of gastric cancer in females results in unique sex ratio (M/F) pattern: etiologic hypothesis. Gastric Cancer 5: 213-219, 2002.
8) Fernandez E, Gallus S, Bosetti C, et al: Hormone replacement therapy and cancer risk: a systematic analysis from a network of case-control studies. Int J Cancer 105: 408-412, 2003.
9) Frise S, Kreiger N, Gallinger S, et al: Menstrual and reproductive risk factors and risk for gastric adenocarcinoma in women: findings from the canadian national enhanced cancer surveillance system. Ann Epidemiol 16: 908-916, 2006.
10) Kaneko S, Tamakoshi A, Ohno Y, et al: Menstrual and reproductive factors and the mortality risk of gastric cancer in Japanese menopausal females. Cancer Causes Control 14: 53-59, 2003.
11) Lindblad M, Garcia Rodriguez L A, Chandanos E and Lagergren J: Hormone replacement therapy and risks of oesophagea and gastric adenocarcinomas. Br J Cancer 94: 136-141, 2006.
12) Lindblad M, Ye W, Rubio C and Lagergren J: Estrogen and risk of gastric cancer: a protective effect in a nationwide cohort study of patients with prostate cancer in Sweden. Cancer Epidemiol Biomarkers Prev 13: 2203-2207, 2004.
13) Chandanos E, Lindblad M, Jia C, et al: Tamoxifen exposure and risk of oesophageal and gastric adenocarcinoma: a population-based cohort study of breast cancer patients in Sweden. Br J Cancer 95: 118-122, 2006.
14) Matsuyama Y, Tominaga T, Nomura Y, et al: Second cancers after adjuvant tamoxifen therapy for breast cancer in Japan. Ann Oncol 11: 1537-1543, 2000.
15) Duell E J, Travier N, Lujan-Barroso L, et al: Menstrual and reproductive factors, exogenous hormone use, and gastric cancer risk in a cohort of women from the European Prospective Investigation Into Cancer and Nutrition. Am J Epidemiol 172: 1384-1393, 2010.
16) Cesarone G, Garofalo C, Abrams M T, Igoucheva O, Alexeev V, Yoon K, Surmacz E, Wickstrom E. RNAi-mediated silencing of insulin receptor substrate 1 (IRS-1) enhances tamoxifen-induced cell death in MCF-7 breast cancer cells. J Cell Biochem. 2006 May 15; 98(2):440-50.
17) Butler W B, Kelsey W H, Goran N. Effects of serum and insulin on the sensitivity of the human breast cancer cell line MCF-7 to estrogen and antiestrogens. Cancer Res. 1981 January; 41(1):82-8.
18) Mauvais-Jarvis F, Clegg D J, Hevener A L. The role of estrogens in control of energy balance and glucose homeostasis. Endocr Rev. 2013 June; 34(3):309-38.
19) Kang L, Zhang X, Xie Y, Tu Y, Wang D, Liu Z, Wang Z Y. Involvement of estrogen receptor variant ER-alpha36, not GPR30, in nongenomic estrogen signaling. Mol Endocrinol. 2010 April; 24(4):709-21.
20) Rao J, Jiang X, Wang Y, Chen B. Advances in the understanding of the structure and function of ER-α36, a novel variant of human estrogen receptor-alpha. J Steroid Biochem Mol Biol. 2011 November; 127(3-5):231-7.
21) Wang J, Li J, Fang R, Xie S, Wang L, Xu C. Expression of ER-α36 in gastric cancer samples and in their matched normal tissues. Oncol Lett. 2012 January; 3(1):172-175.
22) White C, Li C, Yang J, Petrenko N B, Madesh M, Thompson C B, Foskett J K. The endoplasmic reticulum gateway to apoptosis by Bcl-X(L) modulation of the InsP3R. Nat Cell Biol. 2005 October; 7(10):1021-8.
23) Nilsson B O, Olde B, Leeb-Lundberg L M. G protein-coupled oestrogen receptor 1 (GPER1)/GPR30: a new player in cardiovascular and metabolic oestrogenic signalling. Br J Pharmacol. 2011 July; 163(6):1131-9.
24) Mårtensson U E, Salehi S A, Windahl S, Gomez M F, Swärd K, Daszkiewicz-Nilsson J, Wendt A, Andersson N, Hellstrand P, Grände P O, Owman C, Rosen C J, Adamo M L, Lundquist I, Rorsman P, Nilsson B O, Ohlsson C, Olde B, Leeb-Lundberg L M. Deletion of the G protein-coupled receptor 30 impairs glucose tolerance, reduces bone growth, increases blood pressure, and eliminates estradiol-stimulated insulin release in female mice. Endocrinology. 2009 February; 150(2):687-98.
25) Mocellin S, Pilati P, Briarava M, Nitti D. Breast Cancer Chemoprevention: A Network Meta-Analysis of Randomized Controlled Trials. J Natl Cancer Inst. 2015 Nov. 18; 108(2). pii: djv318.
26) Lin Shi, Lingyan Wang, Beibei Wang, Sanda Maria Cretoiu, Qun Wang, Xiangdong Wang and Chengshui Chen. Regulatory mechanisms of betacellulin in CXCL8 production from lung cancer cells. Journal of Translational Medicine 2014, 12:70.

27) Nehra R, Riggins R B, Shajahan A N, Zwart A, Crawford A C, Clarke R. BCL2 and CASP8 regulation by NF-kappaB differentially affect mitochondrial function and cell fate in antiestrogen-sensitive and -resistant breast cancer cells. FASEB J. 2010 June; 24(6):2040-55.

28) Gennari L. Lasofoxifene: a new type of selective estrogen receptor modulator for the treatment of osteoporosis. Drugs Today (Barc). 2006 June; 42(6):355-67.

29) Ke H Z, Paralkar V M, Grasser W A, Crawford D T, Qi H, Simmons H A, Pirie C M, Chidsey-Frink K L, Owen T A, Smock S L, Chen H K, Jee W S, Cameron K O, Rosati R L, Brown T A, Dasilva-Jardine P, Thompson D D. Effects of CP-336,156, a new, nonsteroidal estrogen agonist/antagonist, on bone, serum cholesterol, uterus and body composition in rat models. Endocrinology. 1998 April; 139(4):2068-76.

30) Kelly M J, Levin E R. Rapid actions of plasma membrane estrogen receptors. Trends Endocrinol Metab. 2001 May-June; 12(4):152-6.

31) Shibata Y, Voeltz G K, Rapoport T A. Rough sheets and smooth tubules. Cell. 2006 Aug. 11; 126(3):435-9.

32) Bravo R, Vicencio J M, Parra V, Troncoso R, Munoz J P, Bui M, Quiroga C, Rodriguez A E, Verdejo H E, Ferreira J, Iglewski M, Chiong M, Simmen T, Zorzano A, Hill J A, Rothermel B A, Szabadkai G, Lavandero S. Increased ER-mitochondrial coupling promotes mitochondrial respiration and bioenergetics during early phases of ER stress. J Cell Sci. 2011 Jul. 1; 124 (13): 2143-52.

33) Prossnitz E R, Barton M. Estrogen biology: new insights into GPER function and clinical opportunities. Mol Cell Endocrinol. 2014 May 25; 389(1-2):71-83.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating cancer in an individual comprising administering to the individual an effective amount of lasofoxifene, or a pharmaceutically acceptable salt thereof, wherein the cancer is an ER-α36 positive cancer.

2. The method of claim 1, wherein the cancer is a solid tumor selected from the group consisting of breast cancer, uterine endometrial cancer, lung cancer, gastric cancer, colon cancer, pancreatic cancer, thyroid cancer and liver cancer.

3. The method of claim 2, wherein the cancer is a breast cancer.

4. The method of claim 3, wherein the cancer is a tamoxifen-resistant breast cancer.

5. The method of claim 3, wherein the cancer is a triple negative breast cancer.

6. The method of claim 1, wherein the cancer is an EGFR positive cancer.

7. The method of claim 6, wherein the cancer is an EGFR positive lung cancer.

8. The method of claim 6, further comprising administering to the individual an EGFR kinase inhibitor.

9. The method of claim 8, wherein lasofoxifene or pharmaceutically acceptable salt thereof and the EGFR kinase inhibitor are administered simultaneously or sequentially.

10. The method of claim 8, wherein the EGFR kinase inhibitor is gefitinib, erlotinib, icotinib, afatinib, neratinib, dacomitinib, osimertinib, rociletinib orolmutinib, or a pharmaceutically acceptable salt thereof.

11. The method of claim 1, wherein the cancer is a HER2 positive cancer.

12. The method of claim 11, wherein the cancer is a HER2 positive breast cancer or a HER2 positive gastric cancer.

13. The method of claim 11, further comprising administering to the individual an HER2 inhibitor.

14. The method of claim 13, wherein lasofoxifene or pharmaceutically acceptable salt thereof and the HER2 inhibitor are administered simultaneously or sequentially.

15. The method of claim 13, wherein the HER2 inhibitor is trastuzumab pertuzumab, lapatinib or ado-trastuzumab emtansine (T-DM1).

16. The method of claim 1, wherein ER-α36 expression in the cancer is determined by presence of an ER-α36 peptide.

17. The method of claim 1, wherein the method comprises administering to the individual an effective amount of lasofoxifene.

18. The method of claim 1, wherein the individual is a human.

19. A kit comprising (i) a composition comprising lasofoxifene or a pharmaceutically acceptable salt thereof; and (ii) an agent for determining presence of an ER-α36 peptide or ER-α36 mRNA.

20. A pharmaceutical composition comprising an effective amount of lasofoxifene, or a pharmaceutically acceptable salt thereof, and at least one additional agent selected from the group consisting of an EGFR kinase inhibitor a functional equivalent thereof and aHER2 inhibitor a functional equivalent thereof.

* * * * *